(12) United States Patent
Gavney, Jr.

(10) Patent No.: US 7,743,448 B2
(45) Date of Patent: Jun. 29, 2010

(54) DEVICE AND SYSTEM WITH MOVING SQUEEGEE FIELDS

(76) Inventor: James A. Gavney, Jr., 725 Wildwood La., Palo Alto, CA (US) 94303

( * ) Notice: Subject to any disclaimer, the term of this patent is extended or adjusted under 35 U.S.C. 154(b) by 949 days.

(21) Appl. No.: 11/207,670

(22) Filed: Aug. 19, 2005

(65) Prior Publication Data

US 2005/0273954 A1    Dec. 15, 2005

Related U.S. Application Data

(63) Continuation-in-part of application No. 10/692,837, filed on Oct. 24, 2003, now Pat. No. 7,181,799, which is a continuation-in-part of application No. 10/382,559, filed on Mar. 5, 2003, now Pat. No. 6,820,299, which is a continuation of application No. 09/588,686, filed on Jun. 5, 2000, now Pat. No. 6,571,417, which is a continuation-in-part of application No. 09/330,704, filed on Jun. 11, 1999, now Pat. No. 6,319,332, said application No. 10/692,837.

(60) Provisional application No. 60/439,317, filed on Jan. 10, 2003, provisional application No. 60/463,347, filed on Apr. 15, 2003.

(51) Int. Cl.
 *A61C 17/22* (2006.01)
(52) U.S. Cl. .............. 15/22.1; 15/28; 15/117
(58) Field of Classification Search ............ 15/22.1, 15/22.2, 28, 117
See application file for complete search history.

(56) References Cited

U.S. PATENT DOCUMENTS

| 34,109 A | 1/1862 | Fenshaw et al. |
|---|---|---|
| 66,834 A | 7/1867 | Harlan |
| 104,886 A | 6/1870 | Rhodehamel |
| 116,030 A | 6/1871 | Devines |
| 116,340 A | 6/1871 | O'Brian |
| 218,431 A | 8/1879 | Dunham |
| 411,910 A | 10/1889 | Van Horne |

(Continued)

FOREIGN PATENT DOCUMENTS

CH    172320    12/1934

(Continued)

OTHER PUBLICATIONS

"A new high-performance manual toothbrush" Supported by the Colgate-Palmolive Company, 2004 Medical World Business Press, Inc.

(Continued)

*Primary Examiner*—Randall Chin
(74) *Attorney, Agent, or Firm*—James A. Gavney, Jr.; JAG Patent Services LLC

(57) ABSTRACT

A device with moving squeegees is disclosed. The squeegees can have any number of squeegee configurations. The squeegee or groups of the squeegees are configured to move independently or separately concerted fashion. The device is preferably and oral-care device and can include bristles and/or nodules that move or are stationary. In accordance with the embodiments of the invention the oral-care device includes rows of squeegees that move with a first motion and a center section with squeegees, bristles and/or nodules that move with a second motion in a direction and/or frequency that is different from the first motion.

15 Claims, 15 Drawing Sheets

U.S. PATENT DOCUMENTS

| | | | |
|---|---|---|---|
| 742,639 A | 10/1903 | Harlan | |
| 907,842 A | 12/1908 | Meuzies | |
| 915,251 A | 3/1909 | Vanderslice | |
| 1,006,630 A | 10/1911 | Clarke | |
| 1,128,139 A | 2/1915 | Hoffman | |
| 1,142,698 A | 6/1915 | Grove et al. | |
| 1,188,823 A | 6/1916 | Plank | |
| 1,191,556 A | 7/1916 | Blake | |
| 1,268,544 A | 6/1918 | Cates | |
| 1,297,272 A | 3/1919 | Strang et al. | |
| 1,405,279 A | 1/1922 | Cassedy | |
| 1,500,274 A | 7/1924 | Scarling | |
| 1,526,267 A | 2/1925 | Dessau | |
| 1,577,751 A * | 3/1926 | Paschall | 601/112 |
| 1,578,074 A | 3/1926 | Chandler | |
| 1,588,785 A | 6/1926 | Van Sant | |
| 1,598,224 A | 8/1926 | Van Sant | |
| 1,705,249 A | 3/1929 | Henry | |
| 1,707,118 A | 3/1929 | Goldberg | |
| 1,720,017 A | 7/1929 | Touchstone | |
| 1,766,529 A | 6/1930 | Peirson | |
| 1,833,555 A | 11/1931 | Bell et al. | |
| 1,852,480 A | 4/1932 | Ruetz | |
| 1,868,893 A | 7/1932 | Gentle | |
| 1,910,414 A | 5/1933 | Varga | |
| 1,924,152 A | 8/1933 | Coney et al. | |
| 1,965,009 A | 7/1934 | Stevens | |
| 1,993,662 A | 3/1935 | Green | |
| 1,993,763 A | 3/1935 | Touchstone | |
| 2,008,636 A | 7/1935 | Brynan | |
| 2,042,239 A | 5/1936 | Planding | |
| 2,059,914 A | 11/1936 | Rosenberg | |
| 2,088,839 A | 8/1937 | Coney et al. | |
| 2,117,174 A | 5/1938 | Jones | |
| 2,129,082 A | 9/1938 | Byrer | |
| 2,139,245 A | 12/1938 | Ogden | |
| 2,144,408 A | 1/1939 | Holmes | |
| 2,154,846 A | 4/1939 | Heymann et al. | |
| 2,164,219 A | 6/1939 | McGerry | |
| 2,219,753 A | 10/1940 | Seguin | |
| 2,226,145 A | 12/1940 | Smith | |
| 2,244,699 A | 6/1941 | Hosey | |
| 2,279,355 A | 4/1942 | Wilensky | |
| 2,312,828 A | 3/1943 | Adamsson | |
| 2,321,333 A | 6/1943 | Terry | |
| 2,334,796 A | 11/1943 | Steinmetz et al. | |
| 2,443,461 A | 6/1948 | Kempster | |
| 2,516,491 A | 7/1950 | Swastek | |
| 2,518,765 A | 8/1950 | Ecker | |
| 2,534,086 A | 12/1950 | Vosbikian et al. | |
| 2,545,814 A | 3/1951 | Kempster | |
| 2,587,382 A | 2/1952 | Pyne | |
| 2,637,870 A | 5/1953 | Cohen | |
| 2,644,974 A | 7/1953 | Anderson | |
| 2,702,914 A | 3/1955 | Kittle et al. | |
| 2,706,980 A * | 4/1955 | Kahn | 601/103 |
| 2,715,745 A | 8/1955 | Jacobsen | |
| 2,757,668 A | 8/1956 | Meyer-Saladin | |
| 2,807,820 A | 10/1957 | Dinhofer | |
| 2,815,601 A | 12/1957 | Hough, Jr. | |
| 2,875,458 A | 3/1959 | Tsuda | |
| 2,884,151 A | 4/1959 | Biederman | |
| 2,946,072 A | 7/1960 | Filler et al. | |
| 2,987,742 A | 6/1961 | Kittle et al. | |
| 3,103,027 A | 9/1963 | Birch | |
| 3,110,052 A | 11/1963 | Whitman | |
| 3,133,546 A | 5/1964 | Dent | |
| 3,181,193 A | 5/1965 | Nobles et al. | |
| 3,195,537 A | 7/1965 | Blasi | |
| 3,230,562 A | 1/1966 | Birch | |
| 3,231,925 A | 2/1966 | Conder | |
| 3,261,354 A | 7/1966 | Shpuntoff | |
| 3,359,588 A | 12/1967 | Kobler | |
| 3,400,417 A | 9/1968 | Moret | |
| 3,491,396 A | 1/1970 | Eannarino et al. | |
| 3,553,759 A | 1/1971 | Kramer et al. | |
| 3,563,233 A | 2/1971 | Bodine | |
| 3,570,726 A | 3/1971 | Pomodoro | |
| 3,641,610 A | 2/1972 | Lewis, Jr. | |
| 3,939,522 A | 2/1976 | Shimizu | |
| 3,969,783 A | 7/1976 | Shipman | |
| 3,977,084 A | 8/1976 | Sloan | |
| 3,992,747 A | 11/1976 | Hufton | |
| 3,993,052 A * | 11/1976 | Miyahara | 601/87 |
| 4,090,647 A | 5/1978 | Dunning | |
| 4,115,893 A | 9/1978 | Nakata et al. | |
| 4,128,910 A | 12/1978 | Nakata et al. | |
| 4,167,794 A | 9/1979 | Pomeroy | |
| 4,277,862 A | 7/1981 | Weideman | |
| 4,288,883 A | 9/1981 | Dolinsky | |
| 4,428,091 A | 1/1984 | Janssen | |
| 4,458,374 A | 7/1984 | Hukuba | |
| 4,573,920 A | 3/1986 | d'Argembeau | |
| 4,585,416 A | 4/1986 | DeNiro et al. | |
| 4,610,043 A | 9/1986 | Vezjak | |
| 4,691,405 A | 9/1987 | Reed | |
| 4,727,986 A | 3/1988 | Feldstein | |
| 4,763,380 A | 8/1988 | Sandvick | |
| 4,812,070 A | 3/1989 | Marty | |
| 4,827,551 A | 5/1989 | Maser et al. | |
| 4,866,806 A | 9/1989 | Bedford | |
| 4,887,924 A | 12/1989 | Green | |
| 4,913,133 A | 4/1990 | Tichy | |
| 4,929,180 A | 5/1990 | Moreschini | |
| 5,005,246 A | 4/1991 | Yen-Hui | |
| 5,032,082 A | 7/1991 | Herrera | |
| 5,040,260 A | 8/1991 | Michaels | |
| D326,019 S | 5/1992 | Spangler et al. | |
| 5,186,627 A * | 2/1993 | Amit et al. | 433/216 |
| 5,211,494 A | 5/1993 | Baijnath | |
| 5,226,197 A | 7/1993 | Nack et al. | |
| 5,249,327 A | 10/1993 | Hing | |
| 5,283,921 A | 2/1994 | Ng | |
| 5,289,605 A | 3/1994 | Armbruster | |
| 5,335,389 A | 8/1994 | Curtis et al. | |
| 5,341,537 A | 8/1994 | Curtis et al. | |
| 5,429,678 A | 7/1995 | Fany | |
| 5,438,726 A | 8/1995 | Leite | |
| 5,491,863 A | 2/1996 | Dunn | |
| 5,528,793 A | 6/1996 | Schbot | |
| 5,535,474 A | 7/1996 | Salazar | |
| 5,584,690 A | 12/1996 | Maassarani | |
| 5,604,951 A | 2/1997 | Shipp | |
| 5,615,449 A | 4/1997 | Sepke | |
| 5,628,082 A | 5/1997 | Moskovich | |
| 5,669,097 A | 9/1997 | Klinkhammer | |
| 5,689,850 A | 11/1997 | Shekalim | |
| 5,711,759 A | 1/1998 | Smith et al. | |
| 5,735,011 A | 4/1998 | Asher | |
| 5,799,353 A | 9/1998 | Oishi et al. | |
| 5,802,656 A | 9/1998 | Dawson et al. | |
| 5,806,127 A | 9/1998 | Samoil et al. | |
| 5,810,856 A | 9/1998 | Tveras | |
| 5,839,149 A | 11/1998 | Scheier et al. | |
| D402,116 S | 12/1998 | Magloff et al. | |
| D403,510 S | 1/1999 | Menke et al. | |
| 5,896,614 A | 4/1999 | Flewitt | |
| 5,930,860 A | 8/1999 | Shipp | |
| 5,966,771 A | 10/1999 | Stroud | |
| 5,970,564 A | 10/1999 | Inns et al. | |
| 5,980,542 A | 11/1999 | Saldivar | |
| 5,991,959 A | 11/1999 | Raven et al. | |
| 6,000,088 A | 12/1999 | Wright et al. | |
| 6,003,187 A | 12/1999 | Footer et al. | |

| | | | |
|---|---|---|---|
| 6,021,541 A | 2/2000 | Mori et al. | |
| 6,032,313 A | 3/2000 | Tsang | |
| 6,032,322 A | 3/2000 | Forsline | |
| 6,041,467 A | 3/2000 | Roberts et al. | |
| D422,143 S | 4/2000 | Beals et al. | |
| 6,044,514 A | 4/2000 | Kaneda et al. | |
| D424,808 S | 5/2000 | Beals et al. | |
| D425,306 S | 5/2000 | Beals et al. | |
| 6,065,890 A | 5/2000 | Weitz | |
| 6,067,684 A | 5/2000 | Kweon | |
| 6,077,360 A | 6/2000 | Takashima | |
| 6,088,869 A | 7/2000 | Kaneda et al. | |
| 6,092,255 A | 7/2000 | Kim | |
| 6,099,309 A | 8/2000 | Cardarelli | |
| 6,102,923 A * | 8/2000 | Murayama | 606/161 |
| 6,108,854 A | 8/2000 | Dingert | |
| 6,115,871 A | 9/2000 | Royer | |
| 6,126,533 A | 10/2000 | Johnson et al. | |
| 6,151,745 A | 11/2000 | Roberts et al. | |
| 6,151,746 A | 11/2000 | Lewis, Jr. | |
| 6,168,434 B1 | 1/2001 | Bohm-Van Diggelen | |
| 6,182,323 B1 | 2/2001 | Bahten | |
| 6,182,365 B1 | 2/2001 | Tseng et al. | |
| 6,190,367 B1 | 2/2001 | Hall | |
| 6,219,874 B1 | 4/2001 | van Gelder et al. | |
| 6,240,590 B1 | 6/2001 | Nesbit | |
| 6,245,032 B1 | 6/2001 | Sauer et al. | |
| 6,254,390 B1 | 7/2001 | Wagner | |
| 6,272,713 B1 | 8/2001 | Lotwin | |
| 6,276,021 B1 | 8/2001 | Hohlbein | |
| 6,299,508 B1 | 10/2001 | Gagliardi et al. | |
| 6,311,358 B1 | 11/2001 | Soetewey et al. | |
| 6,311,360 B1 | 11/2001 | Lanvers | |
| 6,314,605 B1 | 11/2001 | Solanki et al. | |
| 6,319,332 B1 | 11/2001 | Gavney, Jr. et al. | |
| 6,349,442 B1 | 2/2002 | Cohen et al. | |
| 6,421,867 B1 | 7/2002 | Weihrauch | |
| 6,446,295 B1 | 9/2002 | Calabrese | |
| 6,463,619 B2 | 10/2002 | Gavney, Jr. | |
| 6,510,575 B2 | 1/2003 | Calabrese | |
| 6,513,182 B1 | 2/2003 | Calabrese et al. | |
| 6,553,604 B1 | 4/2003 | Braun et al. | |
| 6,571,417 B1 | 6/2003 | Gavney, Jr. et al. | |
| 6,599,048 B2 | 7/2003 | Kuo | |
| 6,643,886 B2 | 11/2003 | Moskovich et al. | |
| 6,647,585 B1 | 11/2003 | Robinson | |
| D483,184 S | 12/2003 | Geiberger et al. | |
| 6,658,688 B2 | 12/2003 | Gavney, Jr. | |
| 6,658,692 B2 | 12/2003 | Lenkiewicz et al. | |
| 6,668,418 B2 | 12/2003 | Bastien | |
| 6,725,493 B2 | 4/2004 | Calabrese et al. | |
| 6,751,823 B2 | 6/2004 | Biro et al. | |
| 6,813,793 B2 | 11/2004 | Eliav et al. | |
| 6,817,054 B2 | 11/2004 | Moskovich et al. | |
| 6,820,299 B2 | 11/2004 | Gavney, Jr. | |
| 6,820,300 B2 | 11/2004 | Gavney, Jr. | |
| 6,859,969 B2 | 3/2005 | Gavney, Jr. | |
| 6,865,767 B1 | 3/2005 | Gavney, Jr. | |
| 6,886,207 B1 | 5/2005 | Solanki | |
| 6,892,412 B2 | 5/2005 | Gatzemeyer et al. | |
| 6,938,293 B2 * | 9/2005 | Eliav et al. | 15/22.1 |
| 7,213,288 B2 * | 5/2007 | Hohlbein | 15/22.1 |
| 2001/0020314 A1 | 9/2001 | Calabrese | |
| 2001/0039689 A1 | 11/2001 | Gavney, Jr. | |
| 2002/0124337 A1 | 9/2002 | Calabrese et al. | |
| 2002/0138928 A1 * | 10/2002 | Calabrese | 15/22.1 |
| 2003/0033680 A1 | 2/2003 | Davies et al. | |
| 2003/0033682 A1 | 2/2003 | Davies et al. | |
| 2003/0182746 A1 | 10/2003 | Fattori et al. | |
| 2003/0196283 A1 | 10/2003 | Eliav | |
| 2004/0010869 A1 | 1/2004 | Fattori et al. | |
| 2004/0045105 A1 | 3/2004 | Eliav et al. | |
| 2004/0060132 A1 | 4/2004 | Gatzemeyer et al. | |
| 2004/0060133 A1 | 4/2004 | Eliav | |
| 2004/0060134 A1 | 4/2004 | Eliav | |
| 2004/0060135 A1 | 4/2004 | Gatzemeyer et al. | |
| 2004/0060136 A1 | 4/2004 | Gatzemeyer et al. | |
| 2004/0060137 A1 | 4/2004 | Eliav | |
| 2004/0154112 A1 | 8/2004 | Braun et al. | |
| 2004/0200016 A1 | 10/2004 | Chan et al. | |
| 2005/0000048 A1 | 1/2005 | Hohlbein | |
| 2005/0015907 A1 | 1/2005 | Georgi et al. | |
| 2005/0049155 A1 | 3/2005 | Gavney, Jr. et al. | |
| 2005/0060822 A1 | 3/2005 | Chenvainu et al. | |
| 2005/0102780 A1 | 5/2005 | Holbein | |
| 2005/0102783 A1 | 5/2005 | Hohlbein | |
| 2005/0166342 A1 | 8/2005 | Hohlbein | |

FOREIGN PATENT DOCUMENTS

| | | |
|---|---|---|
| DE | 31 14 507 A1 | 3/1983 |
| DE | 298 16 488 U1 | 1/1999 |
| DE | 199 57 639 A1 | 6/2001 |
| EP | 0 435 329 A2 | 9/1989 |
| EP | 0 360 766 A1 | 3/1990 |
| FR | 2 636 818 | 3/1990 |
| FR | 2 793 136 | 11/2000 |
| GB | 214701 | 4/1924 |
| GB | 290515 | 5/1928 |
| GB | 305735 | 2/1929 |
| GB | 620151 | 3/1949 |
| GB | 2 040 161 A | 8/1980 |
| GB | 2 319 170 A | 5/1989 |
| GB | 2 214 420 A | 9/1989 |
| GB | 2 371 217 A | 7/2002 |
| JP | 9-140456 | 3/1997 |
| WO | WO 96/15696 | 5/1996 |
| WO | WO 96/20654 | 7/1996 |
| WO | WO 96/28994 | 9/1996 |
| WO | WO 97/16995 | 5/1997 |
| WO | WO 98/18364 | 5/1998 |
| WO | WO 98/22000 | 5/1998 |
| WO | WO 99/37181 | 7/1999 |
| WO | WO 00/64307 | 8/2000 |
| WO | WO 00/49911 | 11/2000 |
| WO | WO 00/76369 A2 | 12/2000 |
| WO | WO 01/01817 A1 | 1/2001 |
| WO | WO 01/21036 A1 | 3/2001 |
| WO | WO 03/030680 A1 | 4/2003 |
| WO | WO 03/043459 A2 | 5/2003 |
| WO | WO 2004/041023 A2 | 5/2004 |
| WO | WO 2004/064573 A1 | 8/2004 |

OTHER PUBLICATIONS

The Gillette Company, 2004 Annual Report and 2005 Proxy Statement.

* cited by examiner

DEVICE AND SYSTEM WITH MOVING SQUEEGEE FIELDS

RELATED APPLICATIONS

This Application is a Continuation-in-part of application Ser. No. 10/692,837, filed Oct. 24, 2003, and titled "ORAL-CARE DEVICE AND SYSTEM," now U.S. Pat. No. 7,181,799 which is a Continuation-in-part of the application Ser. No. 10/382,559, filed Mar. 5, 2003, and titled "DENTITION CLEANING DEVICE AND SYSTEM," now U.S. Pat. No. 6,820,299 which is a continuation Application of the application Ser. No. 09/588,686, filed Jun. 5, 2000, and titled "DENTITION CLEANING DEVICE AND SYSTEM," now U.S. Pat. No. 6,571,417, which is a Continuation-in-part of the application Ser. No. 09/330,704 filed Jun. 11, 1999, and titled "SQUEEGEE DEVICE AND SYSTEM" now U.S. Pat. No. 6,319,332. The application Ser. No. 10/692,837, filed Oct. 24, 2003, and titled "ORAL-CARE DEVICE AND SYSTEM, now U.S. Pat. No. 7,181,799, the application Ser. No. 10/382,559, filed Mar. 5, 2003, and titled "DENTITION CLEANING DEVICE AND SYSTEM, now U.S. Pat. No. 6,820,299, the application Ser. No. 09/588,686, filed Jun. 5, 2000, and titled "DENTITION CLEANING DEVICE AND SYSTEM," now U.S. Pat. No. 6,571,417 and the application Ser. No. 09/330,704, filed Jun. 11, 1999, and titled "SQUEEGEE DEVICE AND SYSTEM", now U.S. Pat. No. 6,319,332, all hereby incorporated by reference. The application Ser. No. 10/692,837, filed Oct. 24, 2003, now U.S. Pat. No. 7,181,799, and titled "ORAL-CARE DEVICE AND SYSTEM" also claims priority under 35 U.S.C. 119(e) of the U.S. Provisional Patent Application Ser. No. 60/439,317, filed Jan. 10, 2003, and titled "TOOTHBRUSH" and the U.S. Provisional Patent Application Ser. No. 60/463,347, filed Apr. 15, 2003, and titled "SQUEEGEE TOOTHBRUSH." The U.S. Provisional Patent Application Ser. No. 60/439,317 filed Jan. 10, 2003, and titled "TOOTHBRUSH" and the U.S. Provisional Patent Application Ser. No. 60/463,347, filed Apr. 15, 2003, and titled "SQUEEGEE TOOTHBRUSH" are also both hereby incorporated by reference.

FIELD OF THE INVENTION

This invention relates generally to cleaning and applicator devices. More specifically, this invention relates to cleaning and applicator devices with moving squeegee fields.

BACKGROUND

Treating surfaces is an activity that occupies a considerable portion of most peoples time. For example, household surfaces are regularly cleaned and polished and/or require the application of treatment or cleaning materials to the household surfaces. Also, many industrial processes, such as cleaning floors and polishing wafers, require contacting surfaces to clean the surfaces and/or apply materials to the surfaces. Likewise, there are a number of medical and/or personal hygiene activities that require treating surfaces with contact elements to treat or clean the surfaces. A particular example is oral-care, which requires very specialized treatment of a surface in cleaning teeth and gums.

There are a number of different systems and devices available for cleaning teeth and gums. A number of these available systems and devices are inefficient at cleaning teeth and gums and require multiple pass scrubbing with oral cleaning agents, such as tooth pastes or gels, to effectively clean the teeth and gums. Typically, toothbrushes, for example, do not efficiently apply the oral cleaning agents to the teeth and gums and can be abrasive, causing loss of healthy gum tissue and/or damage to teeth. Further, toothbrushes can require a high degree of technique and/or dexterity to be used effectively for cleaning teeth and gums.

What is needed is a dentition cleaning system and device that can efficiently apply oral cleaning agents to teeth and gums and that can clean teeth and gums without a high degree of technique or dexterity. Further, what is needed is a dentition cleaning system and device that is less abrasive to teeth and gums than a conventional bristle toothbrush.

SUMMARY OF THE INVENTION

The present invention is directed to a device comprising a head that is configured to clean surfaces, treat surfaces and/or apply materials to surfaces. Preferably, the head is a cleaning head that is configured to clean and/or treat teeth and gums. However, it will be clear to one skilled in the art that the present invention can equally be applied to devices that are configured to clean any number of different surfaces including, but not limited to, floors, cars, wafers and/or appliances.

The cleaning head can include a support structure or surface that is formed or any suitable material, but is usually a different material or has significantly different physical properties than the squeegees. For example, the support structure or surface can be formed or molded from polyolefins, such as polypropylenes and polyethylenes, polyamides, such as nylons, and polyesters, such as polyethylene terephthalate. Other suitable materials include polymethylmethacrylate, styrene acrylonitrate and cellulose esters, such as cellulose propionate.

In accordance with the present invention, a device comprises a cleaning head with squeegees that are configured to move independently or separately. To move independently or separately, herein means the squeegees move separately from one or more of the other squeegees (the squeegees are separate), but does not necessarily mean that the squeegees are not synchronized to move with a similar or the same motion or that the squeegees are not coupled to the same mechanism to drive the motion of the squeegees. In fact, it is preferable that at least a portion of the squeegees move in a concerted fashion in the same direction of different directions. Preferably, the squeegees are configured to move back and forth, vibrate, rotate, oscillate or otherwise automatically move. In accordance with further embodiments of the invention the cleaning head includes bristles. In still further embodiments of the invention, the cleaning head comprises nodules (i.e., resilient protrusions) with any number of different geometries such as described below and further described in U.S. patent application Ser. No. 09/957,302, filed Sep. 19, 2001, and titled "DEVICE WITH MULTI-STRUCTURAL CONTACT ELEMENTS," now U.S. Pat. No. 6,865,767, the contents of which are hereby incorporated by reference.

The squeegee elements utilized in the present invention can have any number of different geometries including curved, rounded angled, corrugated, pointed and/or textured walls and/or wiping edges. A squeegee is a wiping element that has elongated walls that are longer in one direction that in another or are thicker in one dimension that in another, such as to provide an elongated top wiping edge, which can be contoured, textured or shaped with any number of different geometries. The walls of a squeegee are shorter or have the smaller dimensions are also referred to herein as side wiping edges. Squeegee elements can include squeegee segments with one or more terminus ends (side wiping edges) and/or squeegee segments that form matrices of squeegee compartments and continuous squeegees that encircle portions or regions of the cleaning head.

Squeegees utilized in the present invention can be formed from any number of different materials. In accordance with the embodiments of the invention, squeegees or a portion thereof are formed from a porous material. For example, squeegees are formed from foam, cellulose any other porous or semi-porous polymeric material. The foam or cellulose can be sufficiently dense, and exhibit a relatively low absorbency with respect to water while providing texture to the walls and/or edges of the squeegees. In accordance with still further embodiments of the present invention, squeegees include an abrasive material that is integrated with the material(s) used to form the squeegees and/or is applied to surfaces of squeegee walls and/or edges after they are formed. The squeegees can also be formed from composites of materials. For example, squeegees can be formed from a resilient polymeric material such as silicon, latex, rubber, polyurethane, neoprene or a combination thereof. Other polymer materials, such as a block co-polymer, including styrenes (for example styrene ethylene butadiene styrene, or styrene butadiene styrene), polyolefins (for example polypropylene/ethylene propylene diamine modified systems (i.e. synthetic rubber)), polyamides (for example polyamide (2 or polyamide 6), polyesters (for example polyester ester or polyether ester), polyurethanes (for example polyesterurethane, polyetherurethane or polyesteretherurethane) can also be used. Squeegees can be formed from two materials, which contain an internal phase material in a continuous phase of another material. A particularly preferred example of this is the polypropylene/ethylene propylene diamine modified material described above, which is commercially available as Santroprene PPA (ex Advanced Elastomer Systems). Also two-phase materials can be used, such as a continuous external thermoplastic phase, with the internal phase typically containing particles which may be in the order of 0.5-5 microns across.

Squeegees can have hardness values in a range of 10 to 100 Shores A, as defined in the D2240-00 Standard Test Method for Rubber Property-Durometer Hardness, published by the American Society for Testing Materials, the contents of which are hereby incorporated by reference. Squeegees also preferably exhibit a flexural modulus of 5 Mpa. or more. Additional details of squeegee configurations are provided in the U.S. Pat. No. 6,319,332, titled "SQUEEGEE DEVICE AND SYSTEM," and U.S. Pat. No. 6,571,417, titled "DENTITION CLEANING DEVICE AND SYSTEM," the contents of which are also both hereby incorporated by reference. Squeegees can also be formed from composites of materials. For example, a portion of a squeegee can be formed for rubber-like molded material with alternating sections of a porous or semi-porous foam or a bottom portion of the squeegee can be formed from a molded rubber-like material and the top wiping portion can be formed from a porous or semi-porous foam.

In accordance the embodiments of the invention, a squeegee can include an elongated squeegee segment with smaller fins that protrude from walls of the elongated squeegee segment and provide top wiping edges and side wiping edges, such as described in detail in U.S. patent application Ser. No. 10/454,281, filed Jun. 3, 2003, now U.S. Pat. No. 6,859,969, entitled "MULTI-DIRECTIONAL WIPING ELEMENTS AND DEVICES USING THE SAME", the contents of which are hereby incorporated by reference.

In accordance with yet further embodiments of the invention, the cleaning head includes squeegees and bristles. The bristles can be formed from polyamides such as nylon and/or polyesters such as polybutylene terephthalate. Sections of bristles can be stationary, configured to move or a combination thereof, such as described in detail below.

In accordance with still further embodiments of the invention a cleaning head, in addition to squeegees and/or bristles, includes nodules or nodular protrusions. The nodules or nodular protrusions are formed from a polymeric material or materials including, but not limited to foams, thermoplastic elastomer such as polyetheramides, polyesters, styrene-ethylene-butylenestyrene block copolymers, polyurethanes, polyolefin elastomers, and mixtures thereof.

In accordance with further embodiments of the invention, a system or device comprises a handle which provides power to a motorized cleaning head comprising the regions, such as described above. The cleaning head can be configured to detachably couple to the handle or, alternatively, can be permanently attached to the handle. In accordance with further embodiments of the invention, one or more of the regions can be configured to detachably couple to a support structure of the cleaning head, such that regions, wiping elements, bristles or combinations thereof can be replaced when they are worn out. It will be understood that the handle and/or the cleaning head are configured with any number of moving parts, such as gears, which allow the squeegees to move independently, such as described above. The handle can include a battery or battery pack that can be recharged by docking to a recharging station. The handle can also include a motor and/or other mechanisms for driving the moving action of the squeegee fields either by battery or by plugging the device into a power source, such as an electrical power outlet.

DETAILED DESCRIPTION

Figure 1A:
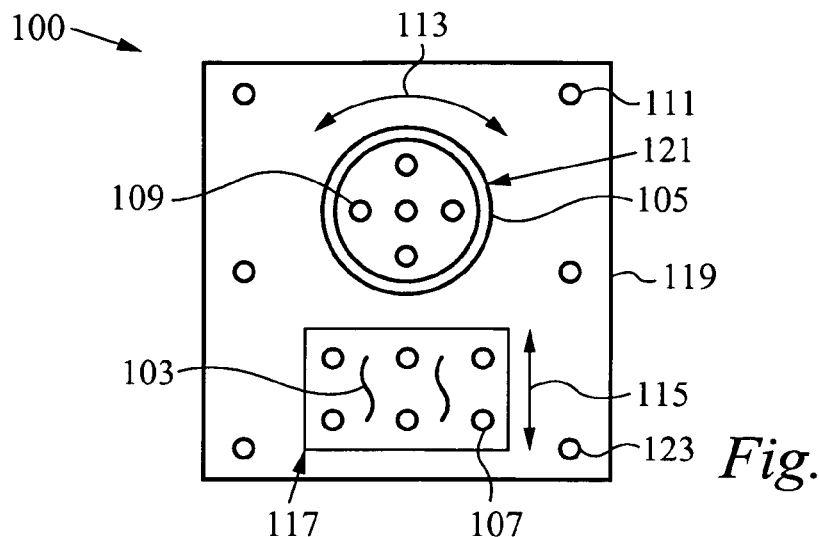
FIGS. 1A-C show cleaning heads with independently movable regions, in accordance with the embodiments of the invention.

FIG. 1A shows a schematic top view of a cleaning head configuration 100, in accordance with the embodiments of the invention. The cleaning head configuration 100 comprises a first region 121 and a second region 117 that are configured to move independently from each other. In accordance with the embodiments of the invention, the first region 121 comprises a continuous squeegee element 105 that encircles a portion of the first region 121 and bristles, bristle tufts and/or nodules 109 protruding therefrom. While FIGS. 1A-C are described as having bristles or bristle tuft, it will be clear to one skilled in the art and from the description below that the cleaning head configuration can include, in place of bristle or bristle tufts or in addition to bristles or bristle tufts, nodules such as those described with reference to FIGS. 6A-H and FIGS. 7A-G below.

Still referring to FIG. 1A, the first region 121 is preferably configured to rotate and/or oscillate, as indicated by the arrow 113, independently from the second region 117, which can be stationary or configured to move, for example in a backward and forward motion as indicated by the arrow 115. The second region 117 preferably comprises bristle, bristle tufts and/or nodules 107 that protrude therefrom and can also include one or more curved squeegee elements or wave-shaped squeegee elements 103. The cleaning head configuration 100 includes a support structure 119 with bristle, bristle tufts and/or nodules 111 and 123 protruding therefrom.

Figure 1B:
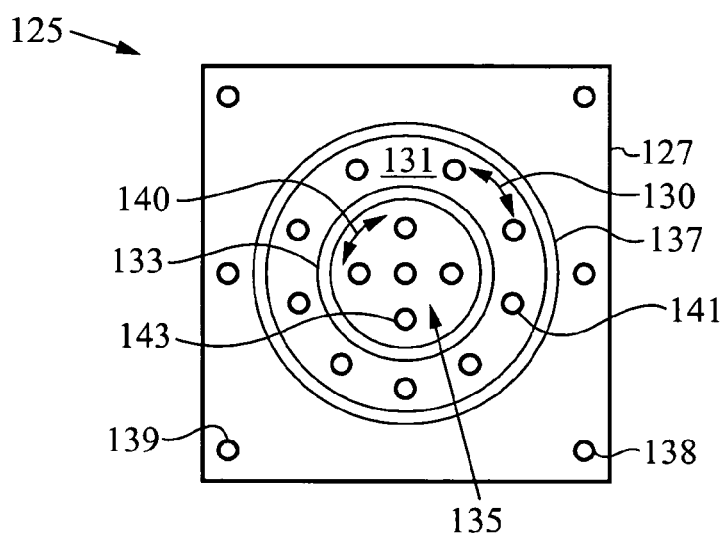
Figure 1C:
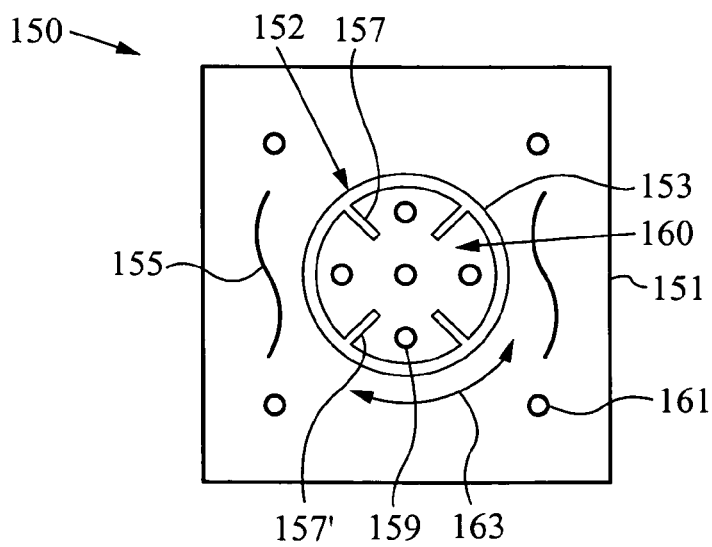

FIG. 1B, shows a schematic top view of a cleaning head configuration 125, in accordance with further embodiments of the invention. The cleaning head configuration 125 comprises a first region 131 and a second region 135 that are configured to move independently from each other. In accordance with this embodiment, the first region 131 comprises a first continuous squeegee 137 that encircles a first set of bristles and/or nodules 141 protruding from the first region 131 and encircles the second region 135. The second region 135 comprises a second continuous squeegee 133 the encircles a second set of bristles and/or nodules 143 protruding from the second region 135. Accordingly, first region 131 can be described as surrounding the second region 135.

Still referring to FIG. 1B, the first region 131 and the second region 135 are preferably configured to rotate and/or oscillate as indicated by the arrows 130 and 140, respectively. In accordance with a preferred embodiment of the invention, the first region 131 and the second region 135 are configured to move in opposite directions while rotating and/or oscillating. It will be clear to one skilled in the art that the first region 131 and the second region 135 can be configured to move in the same direction at the same or at a different rate of rotation and/or oscillation. In accordance the invention, the cleaning head configuration 125 can also have support structure 127 with bristle, bristle tufts and/or nodules 138 and 139 protruding therefrom.

FIG. 1C, shows a schematic top view of a cleaning head configuration 150 in accordance with yet further embodiments of the invention. The cleaning head configuration 150 comprises at least one region 160 that is configured to rotate, oscillate and/or otherwise move in one or more directions, as indicated by the arrow 163. The region 160 preferably includes one or more squeegee elements 152. In accordance with the embodiments of the invention, the squeegee element 152 comprises a primary squeegee segment 153 with squeegee wiping fins 157 and 157' that protrude from an inner wall of the primary squeegee segment 153.

Still referring to FIG. 1C, the primary squeegee segment 153, in accordance the embodiments of the invention, is a continuous segment 153 that encircles at least a portion of the region 160 and bristles, bristle tufts and/or nodules 159 protruding from the encircled portion of the region 160. While the squeegee wiping fins 157 and 157' are shown here as protruding from an inner wall of the continuous primary squeegee segment 153, it will be clear to one skilled in the art that in addition to the squeegee wiping fins 157 and 157' or alternatively to the squeegee wiping fins 157 and 157', the squeegee element 152 can include one or more squeegee wiping fins protruding from an outer wall of the continuous squeegee segment 153. Also, while the primary squeegee segment 153 is shown here as a continuous squeegee segment, any number of geometries are contemplated, such as those described with reference to FIGS. 4A-M below. Squeegee configurations can have squeegee wiping fins with contoured or shaped wiping edges and/or wiping walls. Also, squeegee wiping fins can have wiping edges that protrude to the same or different heights than the wiping edges of a primary squeegee segment to which they are attached. A number of squeegee element configurations that have squeegee wiping fins are described in U.S. patent application Ser. No. 10/454,281, filed Jun. 3, 2003, now U.S. Pat. No. 6,859,969, and titled "MULTI-DIRECTIONAL WIPING ELEMENTS AND DEVICES USING THE SAME," referenced previously.

Figure 2:
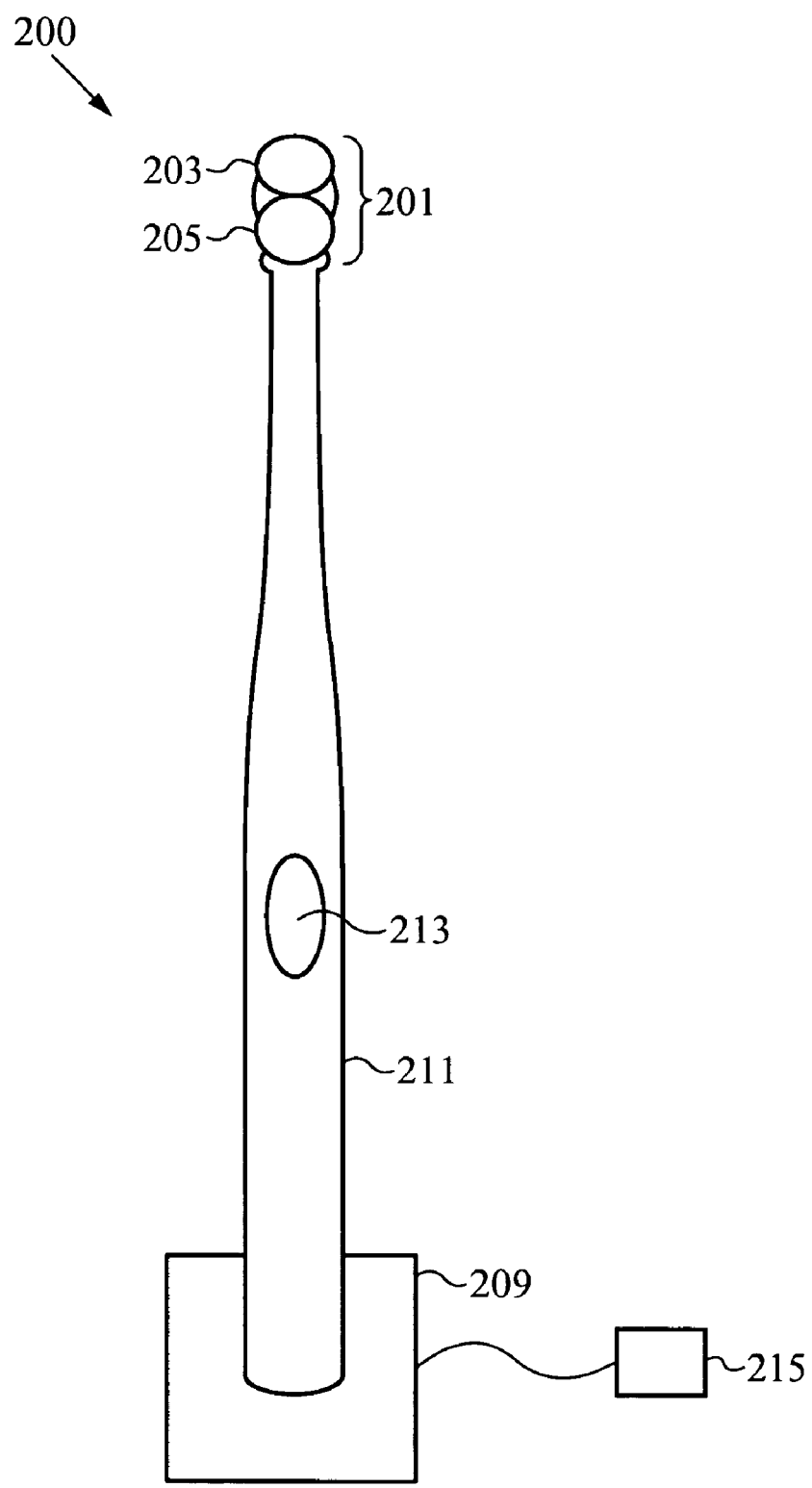
FIG. 2 shows an electric powered oral-care device comprising a power cleaning head with independently movable regions, in accordance with the embodiments of the invention.

FIG. 2 shows an electric powered oral-care apparatus 200 comprising a power cleaning head 201 with independently movable regions 203 and 205 that each includes one or more squeegee elements, such as described with reference to FIGS. 1A-C above and FIGS. 3A-C below. In accordance with the embodiments of the invention, the electric powered oral-care apparatus 200 comprises a power or recharging station 209 for docking a body portion 211 of the oral-care apparatus 200. The power or recharging station 209 comprises means 215 for plugging the power or recharging station 209 into an electrical receptacle and recharging a battery (not shown) housed within the body portion 211 of the oral-care apparatus 200, wherein the battery is configured for providing power to a driver mechanism (not shown) that moves one or both of the regions 203 and 205. Alternatively, or in addition to the power supply mechanism described above, the apparatus 200 can be configured to be powered with disposable batteries (not shown) that are housed in the body portion 211 of the oral-care apparatus 200. Preferably, the oral-care apparatus 200 has a power switch 213 for energizing the power head 201 to move the power cleaning head 201 on or turn it off. Also, the oral-care apparatus 200 can include any number of timer mechanisms to indicate to a user a preferred amount of time to clean teeth and gums with the oral-care apparatus 200. For example, the oral-care apparatus 200 can be configured to automatically shut off in a predetermined period of time after being energized with the power switch 213.

Figure 3A:
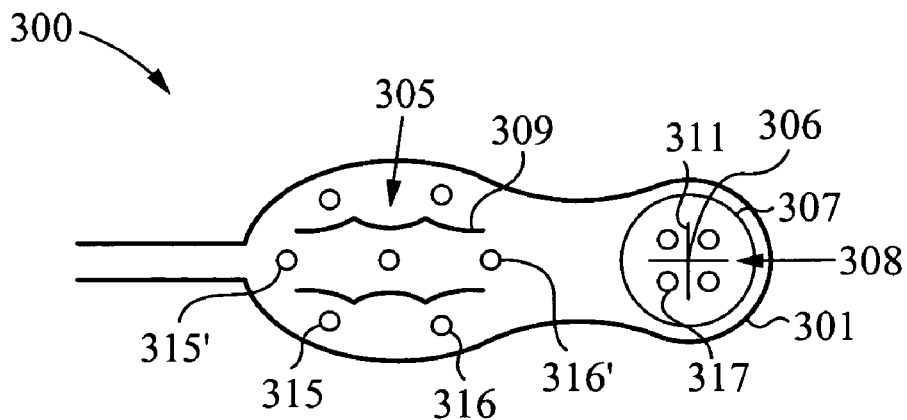
FIGS. 3A-C show oral-care cleaning heads with movable regions comprising squeegee elements, bristles and/or nodules in accordance with the embodiments of the invention.
Figure 3B:
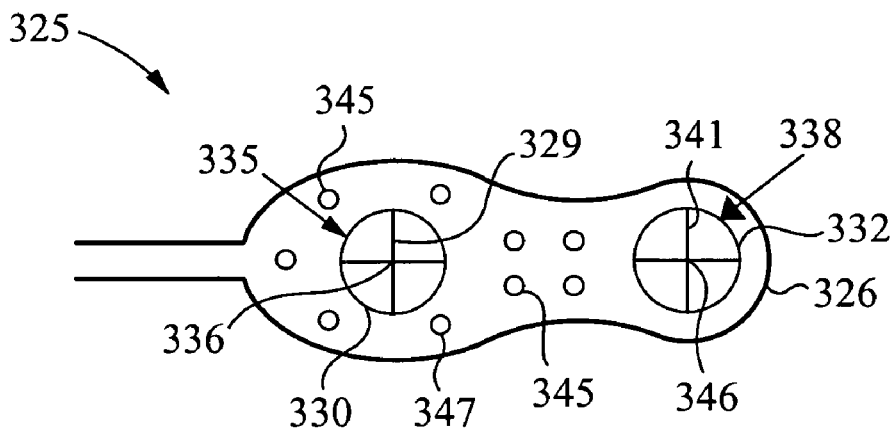
Figure 3C:
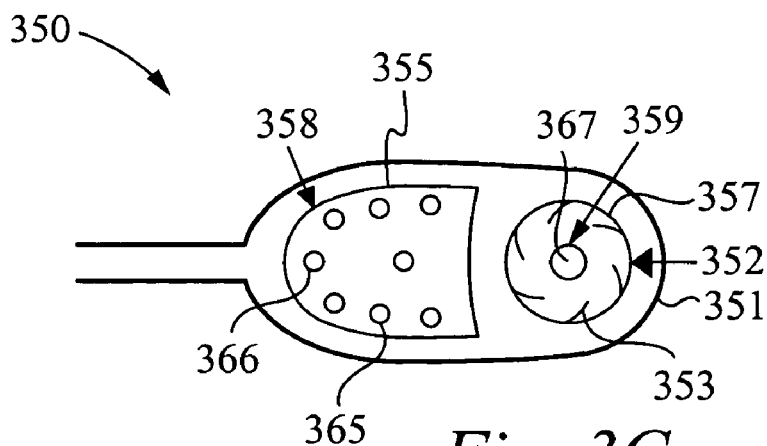

FIGS. 3A-C show oral-care cleaning heads 300, 325 and 350 with movable regions comprising squeegee elements, bristles, nodules and/or combinations thereof, in accordance with the embodiments of the invention. Referring now to FIG. 3A, the oral-care cleaning head 300 comprises a base structure 301 for supporting a first region 305 and a second region 307. The first region 305 comprises one or more squeegee elements 309 protruding therefrom. The squeegee elements 309 are shown here as wave-like, wherein the squeegee elements 309 have curved squeegee walls that extend in a number of directions two or more times (i.e., wave-like). While the squeegee elements 309 are shown with curved or wave-like walls, squeegee elements with linear or straight squeegee walls are also contemplated. Also, as described above walls of the squeegee elements and/or the top wiping squeegee edges of the squeegee elements 309 can be contoured or shaped in any number of different ways. In addition to the squeegee elements 309, the first region 305 can also have one or more tufts of bristles 315 and 315' and/or nodules 316 and 316' protruding therefrom in directions that are the same or different from that of the squeegee element 309.

Still referring to FIG. 3A, the second region 308 of the oral-care cleaning head 300 can comprise a squeegee element 311 protruding therefrom. The squeegee element 311 can have any number of different geometries, but is shown here as a cross-shaped squeegee element 311, with a number of squeegee segments intersecting at a common position 306. The second region 308 of the oral-care cleaning head 300 can also comprise bristle tufts 317 and/or nodules protruding therefrom in directions that are the same or different from that of the squeegee element 311. Also, the second region 308 of the oral cleaning head 300 can comprise a continuous squeegee element 307 encircling a portion of the second region 308, such that the second region 308 is capable of cupping and holding an oral-care solution, paste and/or gel. In operation, the oral-care cleaning solution, paste and/or gel is applied to the oral-care cleaning head 300 and the second region 308 rotates, oscillates, vibrates and/or otherwise moves relative to the first region while cleaning teeth and/or gums.

Referring now to FIG. 3B, the oral-care cleaning head 325 comprises a base structure 326 for supporting a first region 335 and a second region 338. The first region 335 comprises a first squeegee element protruding therefrom. The first squeegee element is shown here having a cross-shaped squeegee segment 329 with a number of squeegee segments intersecting at a common position 336. Also, the first squeegee element can comprise a continuous squeegee wall segment 330 encircling a portion of the first region 335 and the cross-shaped squeegee segment 329, wherein the walls of the cross-shaped squeegee segment 329 intersect with the continuous squeegee wall segment 330 and wherein the first squeegee element is capable of cupping and holding an oral-care solution, paste and/or gel during a cleaning operation. Also, it is noted that the first region 335 can include one or more bristle tufts and/or nodules (not shown) protruding therefrom in directions that are the same or different from that of the first squeegee element.

Still referring to FIG. 3B, the oral-care cleaning head 325 comprises a second region 338 with a second squeegee element protruding therefrom. The second squeegee element is shown here having a cross-shaped squeegee segment 341 with a number squeegee segments intersecting at a common position 346 and a continuous squeegee wall segment 332 encircling a portion of the second region 338 and the cross-shaped squeegee segment 341. In accordance with the embodiments of the invention, the second region 338 can also include one or more bristle tufts and/or nodules (not shown) protruding therefrom and/or the oral-care cleaning head 325 can have one or more bristle tufts 345 protruding and/or nodules 347 protruding from the support structure 326 in directions that are the same or different from that of the first or second squeegee element. In operation, an oral-care cleaning solution, paste and/or gel is applied to the oral-care cleaning head 325, and the first region 335 and the second region 338 rotate, oscillate, vibrate and/or otherwise move independently of each other while cleaning teeth and/or gums. For example, the first region 335 can rotate or oscillate in one direction while the second region 338 can rotate or oscillate in an opposite direction. While the first squeegee element and the second squeegee element are shown here as combinations of cross-shaped segments 329 and 341 and surrounding continuous squeegee segments 330 and 332, respectively, any number of squeegee element geometries and shapes are contemplated including, but not limited to, those described with reference to FIGS. 4A-M.

Referring now to FIG. 3C, the oral-care cleaning head 350 comprises a support structure 351 for supporting a first region 358 and a second region 359. The first region 358 comprises bristles 365 and/or nodules 366 protruding therefrom. The second region 359 comprises a squeegee element 352. The squeegee element 352 preferably comprises a continuous squeegee wall segment 357 that encircles a portion of the second region 359 and squeegee fins 353. The squeegee fins 353 protrude from an inner wall of the continuous squeegee wall segment 357. The squeegee fins 353 can protrude from the continuous squeegee wall segment 357 at any angle suitable for the application at hand and can protrude to the same or a different height from the support structure 351 than the top wiping edges of the continuous squeegee wall segment 357. Squeegee elements with squeegee fins are further described in U.S. patent application Ser. No. 10/454,281, filed Jun. 3, 2003, now U.S. Pat. No. 6,859,969,and titled "MULTI-DIRECTIONAL WIPING ELEMENTS AND DEVICES USING THE SAME", referenced previously.

In operation, an oral-care cleaning solution, paste and/or gel is applied to the oral-care cleaning head 350 and the second region 359 rotates, oscillates, vibrates and/or otherwise moves independently of the first region 358 while cleaning teeth and/or gums. For example, the second region 359 can rotate or oscillate while the first region 358 moves in a back and forth motion and/or vibrates, such as described above with reference to FIGS. 1A-C.

Still referring to FIG. 3C, the oral-care cleaning head 350 can also include a continuous squeegee element 355 that surrounds a portion of the first region 358. Preferably, the second region 359 of the oral cleaning head 350 further comprises one or more bristle tufts or nodules 367 that are surrounded by the continuous squeegee wall segment 357 and that are configured to move along with the squeegee element 352. While the oral-care cleaning heads 300, 325 and 350 have been described as having squeegee elements, bristle, nodules and combinations thereof, it will be clear to one skilled in the art that bristles are not required.

FIGS. 4A-M illustrate top views of squeegee configurations, or portions thereof, in accordance with further embodiments of the invention, wherein intersecting squeegee segments have different lengths, the same lengths, different heights or the same heights to provide top wiping edges and side wiping edges. Squeegee configurations, or portions thereof, as described with reference to FIGS. 4A-M, can include bristles and/or nodules that protrude from a support surface to the same height or different heights as the squeegee wiping edges of the squeegee segments. Also, the squeegee configurations can include bristles and/or nodules that protrude from the support surface at the same angles or different angles from that of the squeegee segments relative to the support surface.

Figure 4A:
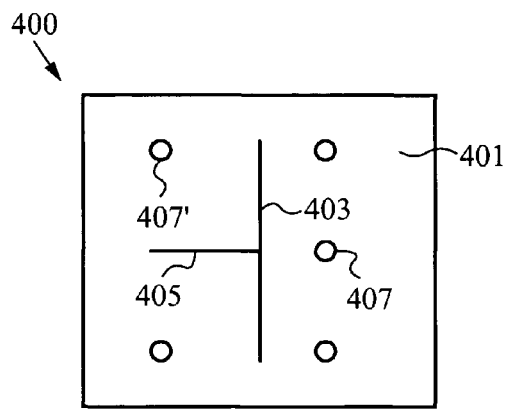
FIGS. 4A-M illustrate top views of portions of cleaning heads with squeegee elements, bristles and/or nodules, in accordance with the embodiments of the invention.

Referring now to FIG. 4A, a squeegee configuration 400, in accordance with the embodiments of the invention, comprises elongated squeegee segments 403 and 405 that intersect and provide top wiping edges and side wiping edges, as explained above. One, or both, of the elongated squeegee segments 403 and 405 protrude from a support surface 401 and can be surrounded or flanked by bristles and/or nodules 407 and 407' that also protrude from the support surface 401 and are preferably configured to wipe a working surface (not shown) simultaneously with the top wiping edges of the elongated squeegee segments 403 and 405.

Figure 4B:
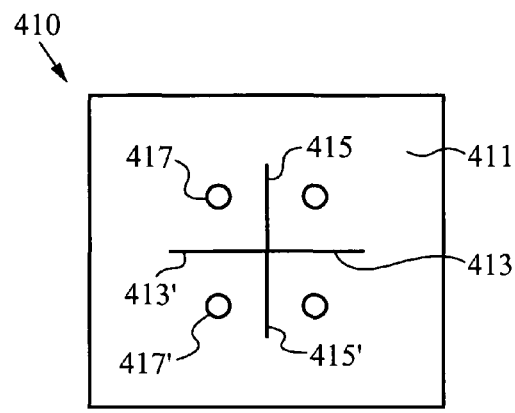

Referring now to FIG. 4B, a squeegee configuration 410, in accordance with the embodiments of the invention, comprises elongated squeegee segments 413, 413', 415 and 415' that intersect and provide top wiping edges that form a cross-shape with side wiping edges. One or more of the elongated squeegee segments 413, 413', 415 and 415' protrude from a support surface 411 and can be surrounded or flanked by bristles or nodules 417 and 417' that also protrude from the support surface 411 and are preferably configured to wipe a working surface (not shown) simultaneously with the top wiping edges of the elongated squeegee segments 413, 413', 415 and 415'.

Figure 4C:
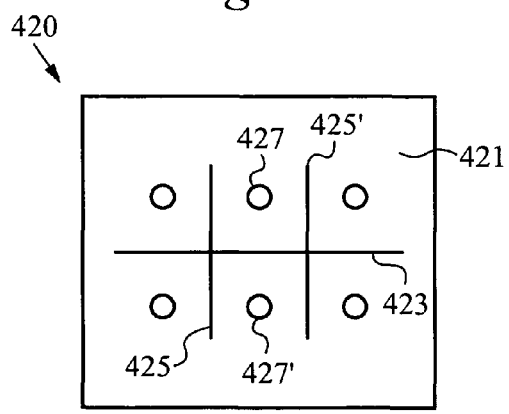

Referring now to FIG. 4C, a squeegee configuration 420, in accordance with the embodiments of the invention, comprises a major elongated squeegee segment 423 and a plurality of minor intersecting squeegee segments 425 and 425' that intersect with a wall of the major elongated squeegee segment 423 to provide cross-like top wiping edges and side wiping edges. One or more of the major squeegee segment 423 and the minor squeegee segments 425 and 425' protrude from a support surface 421 and can be surrounded or flanked by bristles and/or nodules 427 and 427' that also protrude from the support surface 421 and are preferably configured to wipe a working surface (not shown) simultaneously with the top wiping edges of the squeegee segments 423, 425 and 425'.

Figure 4D:
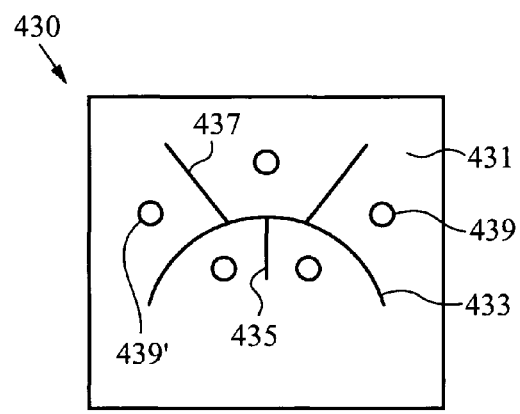

Referring now to FIG. 4D, a squeegee configuration 430, in accordance with the embodiments of the invention, comprises one or more curved squeegee segments 433 and a plurality intersecting squeegee segments 435 and 437. The intersecting squeegee segments 435 and 437 can extend from inside of the curvature of the squeegee segment 433, such as 435, or radiate outward from outside of the curvature of the squeegee segment 433, such as 437, to provide top wiping edges and side wiping edges. The curved squeegee segment 433 and the intersecting squeegee segments 435 and 437 protrude from a support surface 431 and can be surrounded or flanked by bristles and/or nodules 439 and 439' that also protrude from the support surface 431 and are preferably configured to wipe a working surface (not shown) simultaneously with the top wiping edges of the curved 433 and intersecting squeegee segments 435 and 437.

Figure 4E:
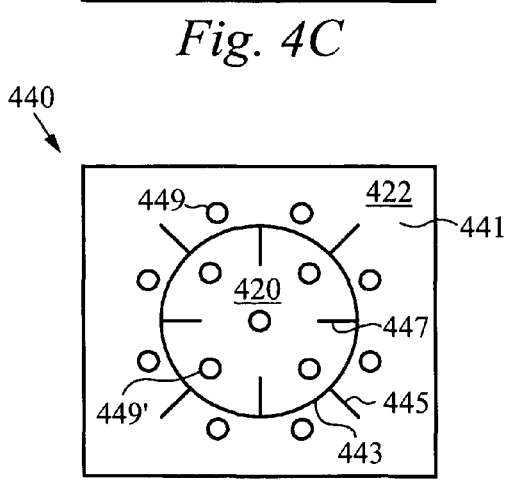

Referring now to FIG. 4E, a squeegee configuration 440, in accordance with the embodiments of the invention, comprises a curved and continuous squeegee segment 443 that forms or bounds an inner squeegee region 420 and an outer squeegee region 422. The squeegee configuration 440 can further comprise intersecting squeegee segments 447 that extend form an inside wall of the curved and continuous squeegee segment 443 and/or intersecting squeegee segments 445 that extend from an outer wall of the curved and continuous squeegee segment 443 to provide top wiping edges and side wiping edges. The curved and continuous squeegee segment 443 and the intersecting squeegee segments 445 and 447 protrude from a support surface 441 and can be surrounded or flanked by bristles and/or nodules 449 and 449' that also protrude from the support surface 441 and are preferably configured to wipe a working surface (not shown) simultaneously with the top wiping edges of the curved and continuous squeegee segment 443 and intersecting squeegee segments 445 and 447.

Figure 4F:
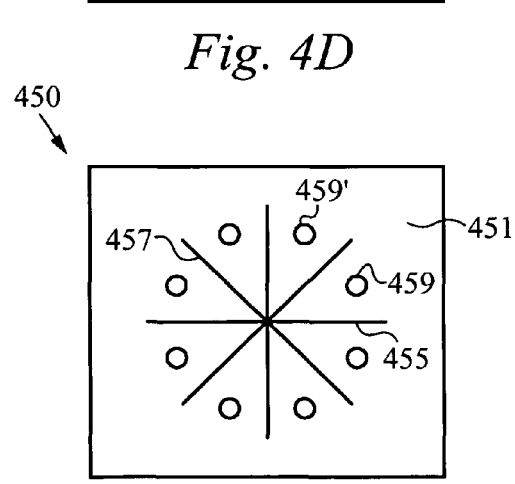

Referring now to FIG. 4F, a squeegee configuration 450, in accordance with the embodiments of the invention, comprises elongated squeegee segments 455 and 457 that intersect and extend at angles less than 90 degrees relative to each other and provide spoke-shaped top wiping edges and side wiping edges. The elongated squeegee segments 455 and 457 protrude from a support surface 451 and can be surrounded or flanked by bristles and/or nodules 459 and 459' that also protrude from the support surface 451 and are preferably configured to wipe a working surface (not shown) simultaneously with the top wiping edges of the elongated squeegee segments 455 and 457.

Figure 4G:
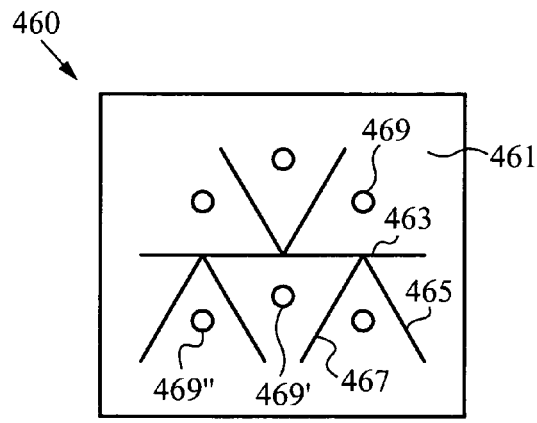

Referring now to FIG. 4G, a squeegee configuration 460, in accordance with the embodiments of the invention, comprises a major squeegee segment 463 and a plurality of minor and intersecting squeegee segments 465 and 467 that intersect a wall of the major squeegee segment 463 and extend from a wall of the major squeegee segment 463 at angles less than or greater than 90 degrees to provide top wiping edges and side wiping edges. The major squeegee segment 463 and the minor squeegee segments 465 and 467 can protrude from a support surface 461 and can be surrounded or flanked by bristles and/or nodules 469, 469' and 469" that also protrude from the support surface 461. The bristle or nodules 469, 469' and 469" are preferably configured to wipe a working surface (not shown) simultaneously with the top wiping edges of the squeegee segments 463, 465 and 467.

Figure 4H:
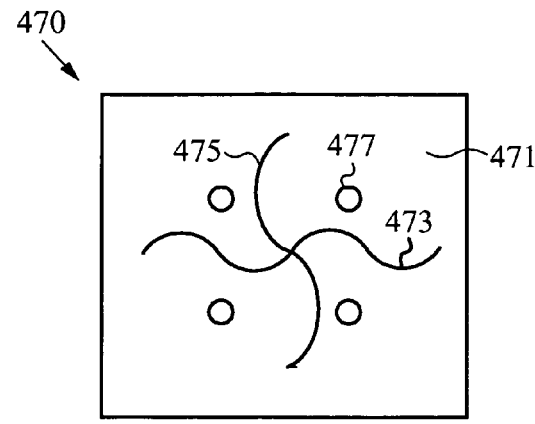

Referring now to FIG. 4H, a squeegee configuration 470, in accordance with the embodiments of the invention, comprises curved squeegee segments 473 and 475 that intersect and provide curved or wave-like top wiping edges and side wiping edges. One or more of the curved squeegee segments 473 and 475, or a portion thereof, protrude from a support surface 471 and can be surrounded or flanked by bristles and/or nodules 477 that also protrude from the support surface 471 and are preferably configured to wipe a working surface (not shown) simultaneously with the top wiping edges of the squeegee segments 473 and 475.

Figure 4I:
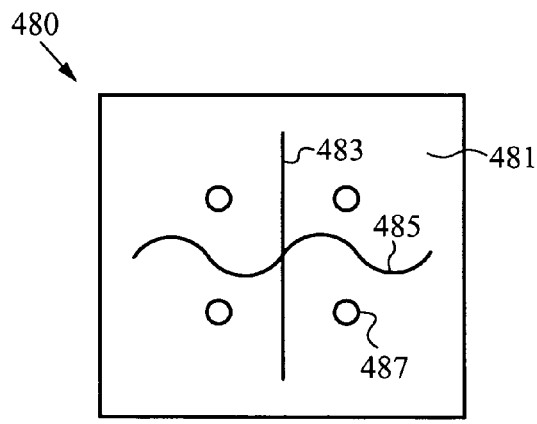

Referring now to FIG. 4I, a squeegee configuration 480, in accordance with the embodiments of the invention, comprises a linear squeegee segment 483 and a curved squeegee segment 485 that intersect and provide linear and curved top wiping edges and side wiping edges. One or more of the squeegee segments 483 and 485, or a portion thereof, protrude from a support surface 481 and can be surrounded or flanked by bristles and/or nodules 487 that also protrude from the support surface 481 and are preferably configured to wipe a working surface (not shown) simultaneously with the linear and curved top wiping edges of the squeegee segments 483 and 485.

Figure 4J:
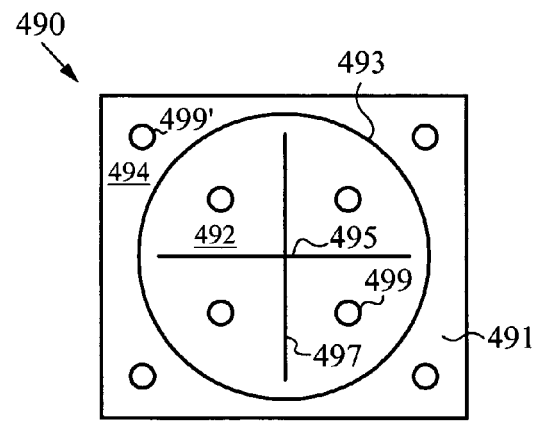

Referring now to FIG. 4J, a squeegee configuration 490, in accordance with the embodiments of the invention, comprises a continuous squeegee segment 493 that forms or bounds an inner squeegee region 492 and an outer squeegee region 494. The continuous squeegee segment 493 has a continuous top wiping edge that encircles or surrounds intersecting squeegee segments 495 and 497. The intersecting squeegee segments 495 and 497 provide cross-shaped top wiping edges and side wiping edges, as explained above. At least a portion of the continuous squeegee segment 493 and one or more of the intersecting squeegee segments 495 and 497 protrude from a support surface 491. Bristles and/or nodules can protrude from the support surface 491 corresponding to the inner squeegee region 492 (as with 499), the outer squeegee region 494 (as with 499') or both, such that the intersecting squeegee segments 495 and 497 and/or the continuous squeegee segment 493 are surrounded or flanked by bristles and/or nodules 499 and 499'. Preferably, the bristles and/or nodules 499 and 499' are configured to wipe a working surface (not shown) simultaneously with the top wiping edges of the squeegee segments 493, 495 and 497.

Figure 4K:
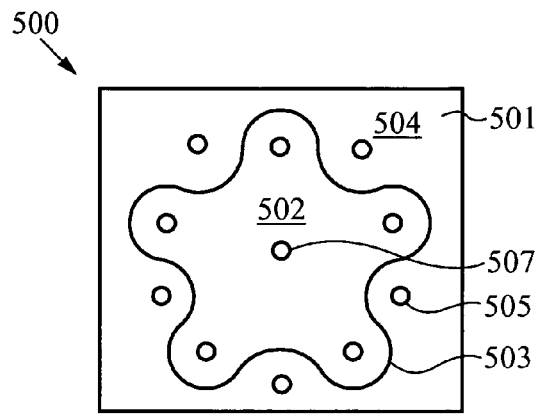

Referring now to FIG. 4K, a squeegee configuration 500, in accordance with the embodiments of the invention, comprises a continuous wave-shaped squeegee segment 503 that forms or bounds an inner squeegee region 502 and an outer squeegee region 504. The continuous wave-shaped squeegee segment 503 can be surrounded or flanked by bristle, bristle sections and/or nodules 505 and 507. Preferably, the bristle, bristle sections and/or nodules 505 and 507 are configured to move and contact a working surface (not shown) simultaneously with the top wiping edge of the continuous wave-shaped squeegee segment 503.

Figure 4L:
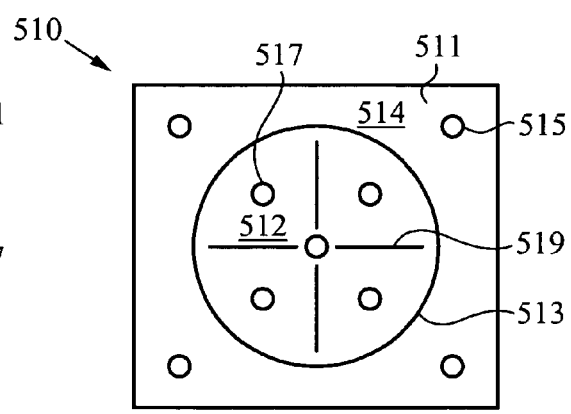

Referring now to FIG. 4L, a squeegee configuration 510, in accordance with the embodiments of the invention, comprises a continuous squeegee 513 that protrudes from a support surface 511 forms or bounds an inner squeegee region 512 and an outer squeegee region 514. The continuous squeegee can be surrounded or flanked by bristles, bristle sections and/or nodules 515 and 517. Preferably, the bristle, bristle sections and/or nodules 515 and 517 are configured to move and contact a working surface (not shown) simultaneously with the top wiping edge of the continuous squeegee 513. The squeegee configuration can also include squeegee segment 519 that protrudes from the inner squeegee region 512. Preferably, the bristles, bristle sections and/or nodules 515 and 517 are configured to wipe the working surface simultaneously with the top wiping edge of the continuous squeegee 513.

Figure 4M:
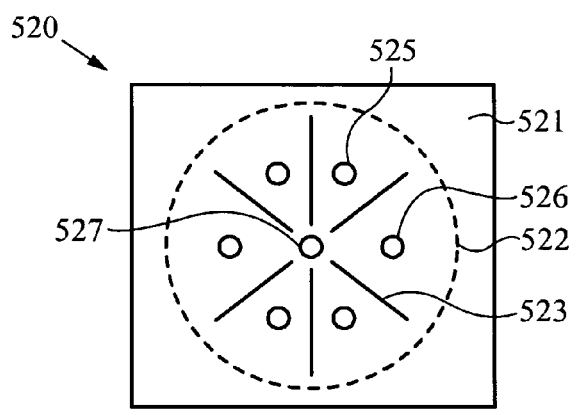

Referring now to FIG. 4M, a squeegee configuration 520, in accordance with the embodiments of the invention, comprises a plurality of squeegee segments 523 protruding form a support surface 521 and extending radially outward from a center 527 of a circle, as indicated by the dotted line 522. The squeegee segments can be surrounded or flanked by bristle, bristle sections and/or nodules 525 and 526. Preferably, the bristle, bristle sections and/nodules 525 and 526 are configured to move and contact a working surface (not shown) simultaneously with the top wiping edges of the squeegee segments 523.

Figure 5A:
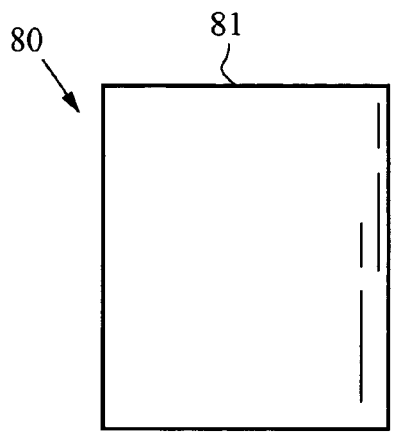
FIGS. 5A-F show several shaped or contoured squeegee edges, in accordance with the embodiments of the invention.
Figure 5B:
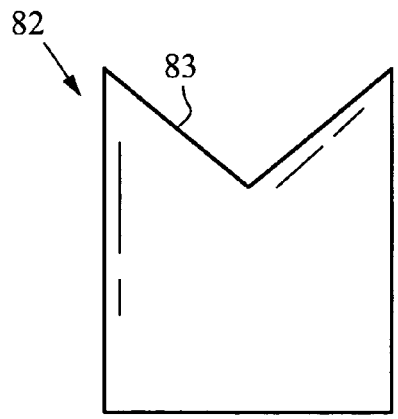
Figure 5C:
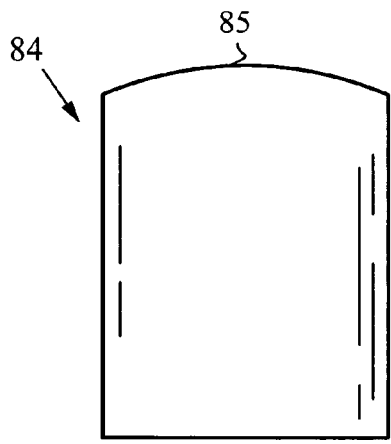
Figure 5D:
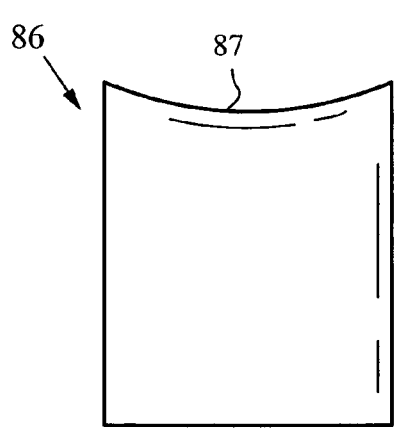
Figure 5E:
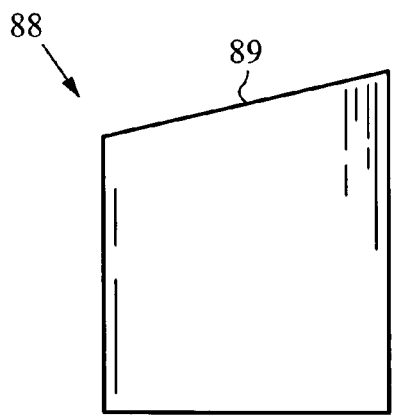
Figure 5F:
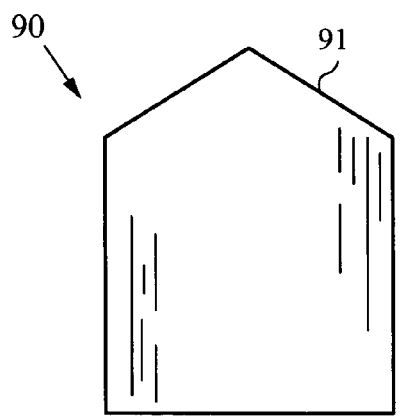

FIGS. 5A-F illustrate several shaped squeegee segments and/or partial structure or squeegee elements, used in the present invention. FIG. 5A shows a squeegee segment 80 with a planar contact edge 81; FIG. 5B shows a squeegee segment 82 with a V-shaped or notched contact edge 83; FIG. 5C shows a squeegee segment 84 with a curve convex contoured contact edge 85; FIG. 5D shows a squeegee segment 86 with a concave contoured contact edge 87; FIG. 5E shows a squeegee segment 88 with a diagonally contoured contact edge 89; and FIG. 5F shows a squeegee segment 90 with a pointed contact edge 91. The shaped squeegee segments described above can be combined in any number of ways to provide elongated squeegee wiping edges used in the oral cleaning device, system and method of the present invention.

Figure 6A:
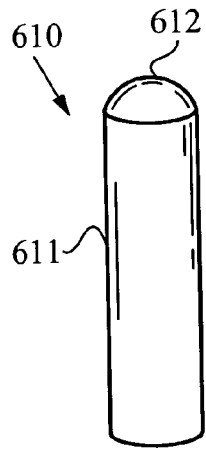
FIGS. 6A-H show nodule structures, in accordance with the embodiments of the invention.
Figure 6B:
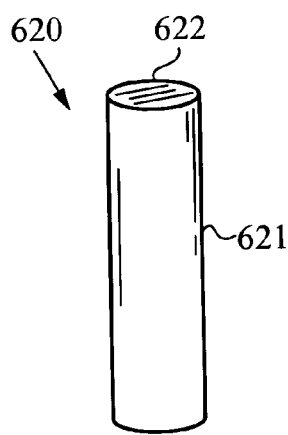
Figure 6C:
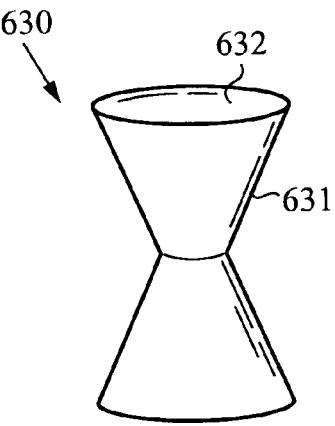
Figure 6D:
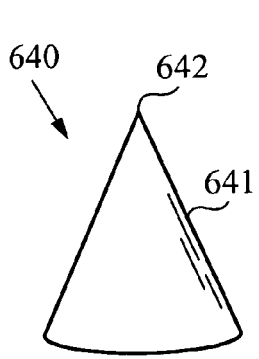
Figure 6E:
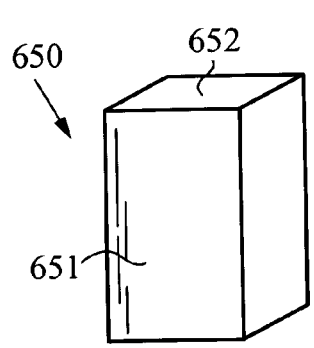
Figure 6F:
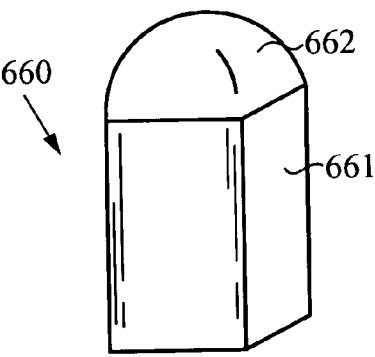
Figure 6G:
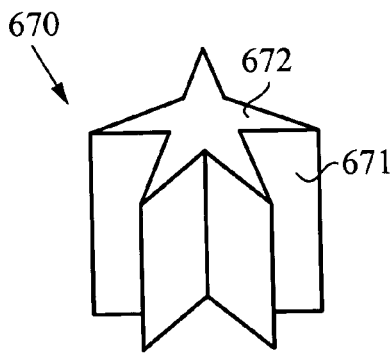
Figure 6H:
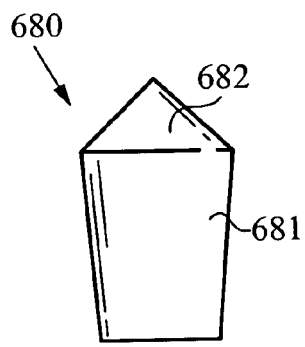

FIGS. 6A-H illustrate several symmetrical nodule structure geometries that are useful in contact devices of the present invention. FIG. 6A shows a nodule 610 with cylindrical protruding walls 611 and a rounded tip portion 612; FIG. 6B shows a nodule 620 with cylindrical protruding walls 621 and a flat top 622; FIG. 6C shows a nodule 630 with contoured protruding walls 631 and a flat top 632; FIG. 6D shows a pointed nodule 660 with tapered protruding walls 641 and a tip 642; FIG. 6E shows a rectangular nodule 650 with planar walls 651 and a flat top 652; FIG. 6F shows a nodule 660 with planar walls 661 and a rounded tip portion 662; FIG. 6G shows a star shaped nodule 670 with protruding walls 671 and a star-shaped top 672; and FIG. 6H shows a triangular nodule 680 with protruding walls 681 and triangular-shaped top 682.

Figure 7A:
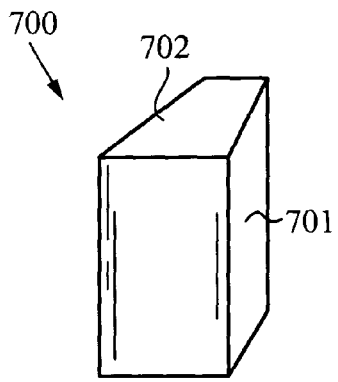
FIGS. 7A-G show alternative nodule structures, in accordance with the embodiments of the invention.
Figure 7B:
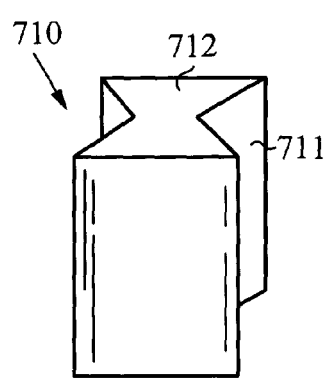
Figure 7C:
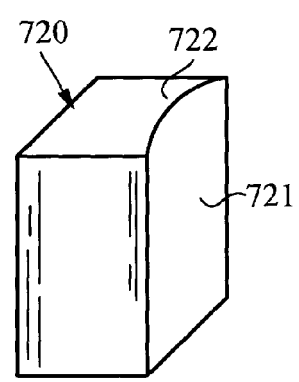
Figure 7D:
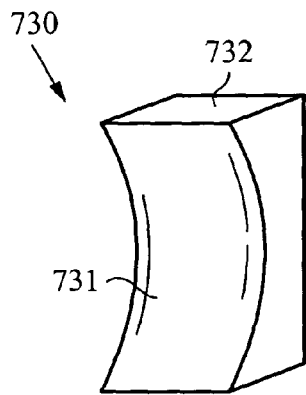
Figure 7E:
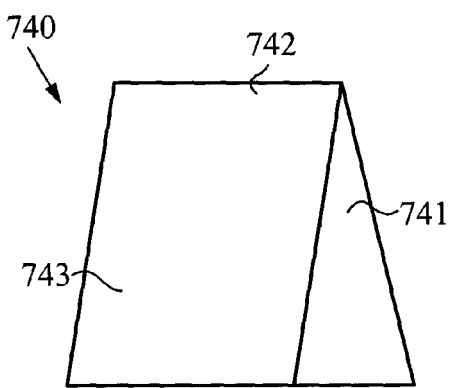
Figure 7F:
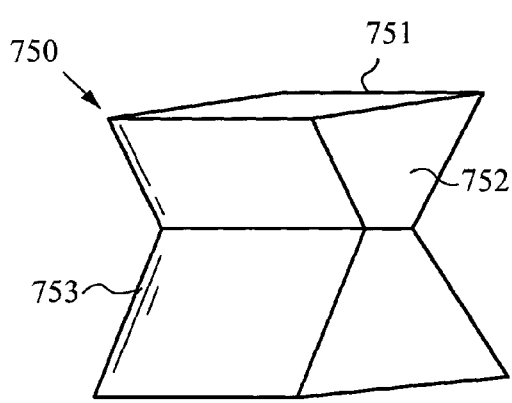
Figure 7G:
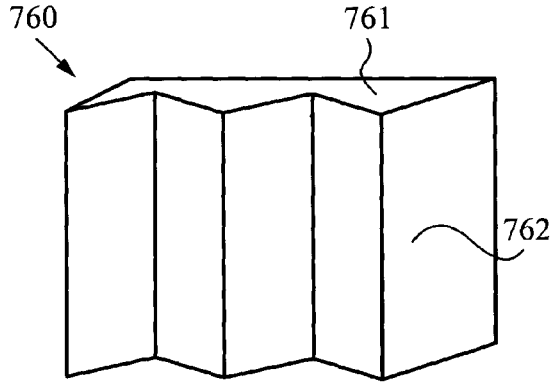

FIGS. 7A-G illustrate several asymmetrical nodule structure geometries that are useful in contact device of the present invention. FIG. 7A shows a wedge-shaped nodule 700 with protruding walls 701 and a top 702; FIG. 7B shows a nodule 710 with contoured walls 711 and a bow-tie shaped top 712; FIG. 7C shows a curved nodule 720 with protruding walls 721 (curved in the elongation direction) and a flat top 722; FIG. 7D shows a curved nodule 730 with protruding walls 731 (curved in the protruding direction) and a top 732; FIG. 7E shows a wedge shaped nodule 740 with tapered walls 743, triangular walls 741 and an edge 742; FIG. 7F shows a nodule 750 with grooved walls 753, bow-tie shaped walls 752 and a flat top 751; and FIG. 7G shows a nodule 760 with contoured walls 762 and a top 761. It will be clear to one skilled in the art that any number of symmetric and asymmetric nodule geometries and combinations thereof are useful in the contact device of the instant invention. Further descriptions of nodule structures and their applications are described in U.S. patent application Ser. No. 09/957,302, filed Sep. 19, 2001, now U.S. Pat. No. 6,865,767,and titled "DEVICE WITH MULTI-STRUCTURAL CONTACT ELEMENTS", referenced previously.

Figure 8:
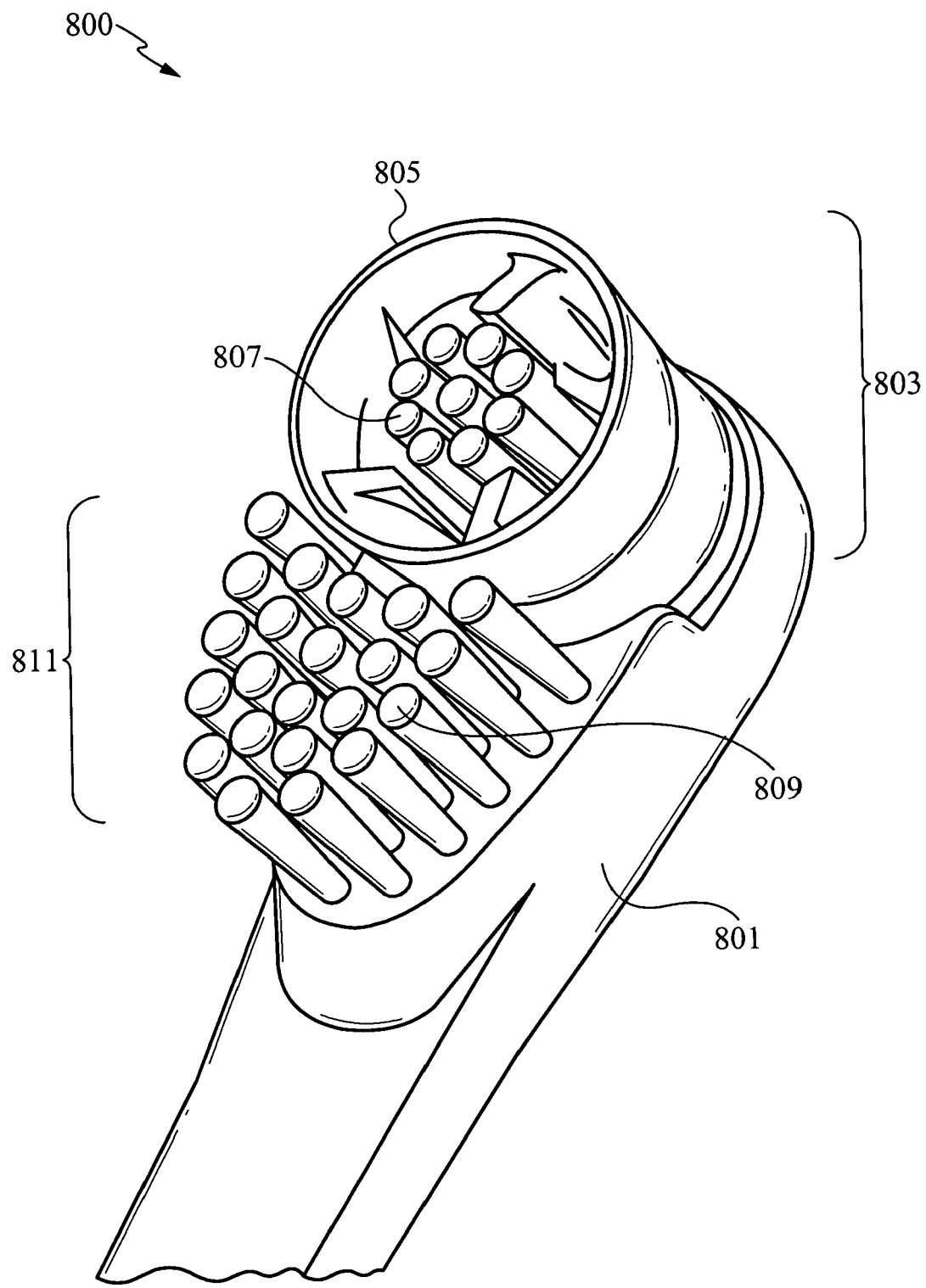
FIG. 8 shows a perspective view of a power head of an oral-care cleaning apparatus, in accordance with the embodiments of the invention.

FIG. 8 shows an oral-care cleaning head 800, in accordance with a preferred embodiment of the invention. The oral-care cleaning head 800 comprises a support structure 801 for supporting a first region 811 and a second region 803. The first region 811 comprises bristle tufts 809 for wiping the surfaces of gums and teeth. The second region 803 comprises a cup-shaped squeegee element 805 that includes a continuous squeegee segment encircling a portion of the second region 803 and squeegee fins protruding from an inner wall of the continuous squeegee segment. The continuous squeegee segment preferably encircles bristle tufts 807 that protrude from the second region for wiping surfaces of teeth and gums.

The first region 811 can be configured to remain stationary or move in any number of ways, as described above, while cleaning teeth and gums. Preferably the cup-shaped squeegee element 805 and the bristle tufts 807 of the second region 803 are configured to oscillate and/or rotate while cleaning teeth and/or gums. The oral-care cleaning head 800, described above is most preferably configured to detachably couple to a power handle, such as described with reference to FIG. 2.

Figure 9A:
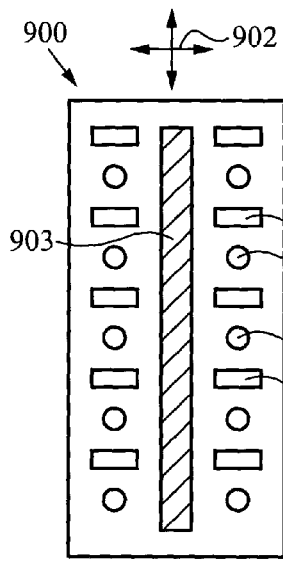
FIGS. 9A-F shows top view of cleaning heads with squeegee fields and bristles and/or nodules, wherein the squeegees are each configured to move independent and in a concerted fashion, in accordance with the embodiments of the invention.

FIGS. 9A-F show top views of cleaning heads with squeegee fields and bristles and/or nodules, wherein the squeegees are configured to move independent and in a concerted fashion, in accordance with the embodiments of the invention. FIG. 9A shows a cleaning head 900 with a plurality of squeegee elements 905 and 905' that extend along opposed sides of and protrude from a support structure 901. The cleaning head 900 also includes a plurality of bristle groups and/or nodules 907 and 907' that protrude from the support structure 901 at positions between the squeegees 905 and 905'. The cleaning head 900 also can include a bristle section 903 that protrudes from the support structure 901 and is positioned between the rows of the squeegees 905 and 905' and the bristle groups and/or nodules 907 and 907'. In operation the squeegees 905 and 905' are configured to move. The squeegees 905 and 905' can be configured to move an any number of directions indicated by arrows 902, but preferably the squeegees are configured to move separately and in a concerted fashion. For example, a portion of the squeegees 905 and 905 can be configured to rotate or oscillate in one direction and another portion of the squeegees 905 and 905' can be configured to rotate or oscillate in an opposite direction at the same time. Preferably, the bristle section 903 is also configured to move. For example, the bristle section 903 can be configured to vibrate, move back and forth or move up and down.

Figure 9B:
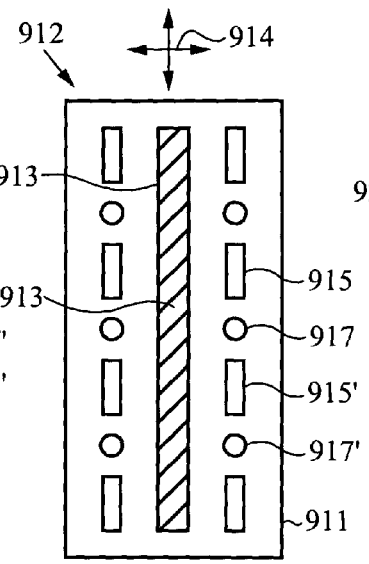

FIG. 9B shows a cleaning head 912 with a plurality of squeegee elements 915 and 915' that extend along opposed sides of and protrude from a support structure 911. The cleaning head 900 also includes a plurality of bristle groups and/or nodules 917 and 917' that protrude from the support structure 911 at positions between the squeegees 915 and 915'. The cleaning head 912 also can include a bristle section 913 that protrudes from the support structure 911 and is positioned between rows of the squeegees 915 and 915' and the bristle groups and/or nodules 917 and 917'. In operation the squeegees 915 and 915' are configured to move. The squeegees 905 and 905' can be configured to move an any number of directions indicated by arrows 914, but preferably the squeegees are configured to move separately and in a concerted fashion. For example, the squeegees 915 and 915' or a portion of the squeegees 915 and 915' are configured to move back and forth, move sideways, vibrate, rotate, oscillate or any combination thereof. Preferably, the bristle section 913 is also configured to move in one or more direction as indicated by the arrows 914.

Figure 9C:
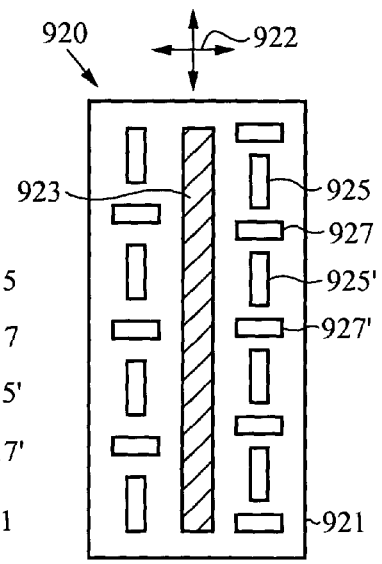

FIG. 9C shows a cleaning head 920 with a first set of squeegee elements 925 and 925' and a second set of squeegee element 927 and 927' that extend along opposed sides of and protrude from a support structure 921. The first set of squeegee elements 925 and 925' and the second set of squeegee element 927 and 927' are elongated at angles with respect to each other and preferably protrude from the support structure 921 in an alternating fashion such as shown. The cleaning head 920 can also include any number of bristle groups and/or nodules (not shown) that protrude from the support structure 921 at positions between the squeegees 925, 925' 927 and 927'. The cleaning head 920 can also include a bristle section 923 that protrudes from the support structure 921 and is positioned between rows of the squeegees 925, 925' 927 and 927". In operation the squeegees 925, 925' 927 and 927', or a portion of the squeegees 925, 925' 927 and 927', move in any number of directions as indicated by arrows 922, but preferably the squeegees are configured to move separately and in a concerted fashion. For example, the squeegees 925, 925' 927 and 927" or a portion of the squeegees 925, 925', 927 and 927' are configured to move back and forth, sideways, vibrate, rotate, oscillate or any combination thereof. Preferably, the bristle section 923 is also configured to move in one or more direction as indicated by the arrows 922.

Figure 9D:
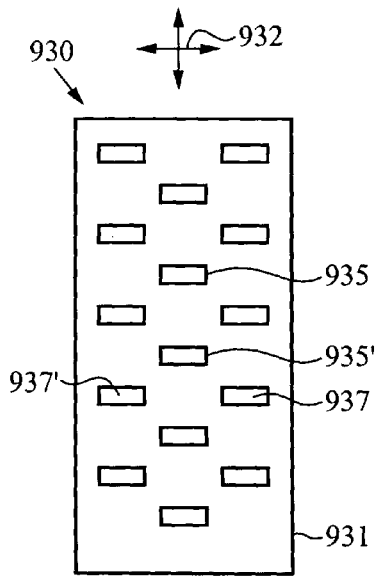

FIG. 9D shows a cleaning head 930 with rows of squeegee elements 937 and 937' that extend along opposed sides of and protrude from a support structure 931. The cleaning head 930 can also include any number of bristle groups and/or nodules (not shown) that protrude from the support structure 931 at positions between the squeegees the rows of squeegees 937 and 937'. The cleaning head 931 can also include a bristle section that protrudes from the support structure 931 (not shown), such as described above. The cleaning head 931 can also include a central row of squeegees 935 and 935' that protrude from the support structure 931 and that are positioned between rows of the squeegees 937 and 937'. In operation the rows of squeegees 937 and 937', or portions of the rows of squeegees 937 and 937', are configured to move in any number of directions as indicated by the arrows 932, but preferably the rows of squeegees 937 and 937', or portions of the rows of squeegees 937 and 937', are configured to move separately and in a concerted fashion. For example, the rows of squeegees 937 and 937', or squeegees within each of the rows of squeegees 937 and 937' are configured to move back and forth, sideways, vibrate, rotate, oscillate or any combination thereof. In further embodiments the central row of squeegees 935 and 935' is also configured to move in one or more direction as indicated by the arrows 932.

Figure 9E:
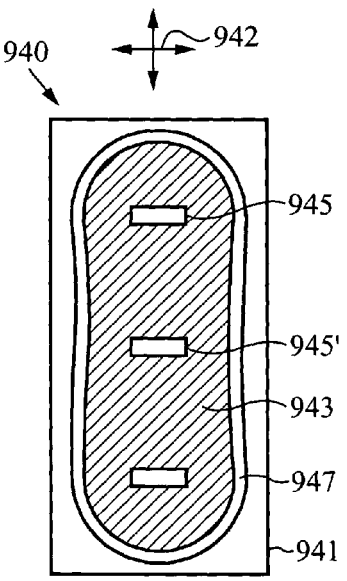

FIG. 9E shows a cleaning head 940 with a row of squeegees 945 and 945' that are surrounded by a bristle field 943 (a group or groupings of bristle tufts) and that protrude from a support structure 941. The cleaning head 940 can also include any number of nodules (not shown) that protrude from the support structure 941 and that are surround by the bristle field 943. The cleaning head 940 can also include continuous squeegee 947 that protrude from the support structure 941 and surrounds the bristle field 943. In operation the squeegees within the row of squeegees 945 and 945', or a portion of the squeegees within the row of squeegees 945 and 945', is configured to move in any number of directions as indicated by the arrows 942, but preferably the squeegees within the row of squeegees 945 and 945' are configured to move separately and in a concerted fashion. The squeegees within the row of squeegees can be configured to move back and forth, sideways, vibrate, rotate, oscillate or any combination thereof. The bristle field 943, or a portion of the bristle field, and/or the continuous squeegee 947 can also be configured to move in one or more directions as indicated by the arrow s922.

Figure 9F:
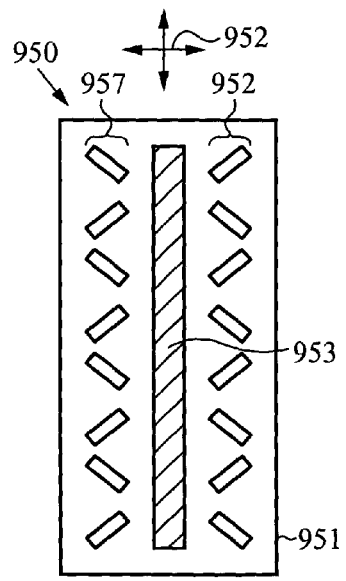

FIG. 9F shows a cleaning head 950, similar to that shown in FIG. 9C. The cleaning head 950 includes a first row of squeegee elements 952 and a second row of squeegee element 957 that extend along opposed sides of and protrude from a support structure 951. The at least a portion of the squeegees of the first row of squeegee elements 955 and a portion of the squeegees of the second row of squeegees 957 are staggered in the elongated direction, such as shown. The cleaning head 950 can also include any number of bristle groups and/or nodules (not shown) that protrude from the support structure 951 at positions between the squeegees of the first row 955 and squeegees of the second row 957. The cleaning head 950 can also include a bristle section 953 that protrudes from the support structure 951 at a positioned between first row 955 and the second row 957 of squeegees. In operation the first row of squeegees 952 and the second row of squeegees 957 move in one or more directions, as indicated by the arrows 952 in a concerted fashion, such as described previously. The first row of squeegees 952 and the second row of squeegees 957 can be configured to move back and forth, sideways, vibrate, rotate, oscillate or any combination thereof. Preferably, the bristle section 953 is also configured to move in one or more direction as indicated by the arrows 952. The squeegees, such as those described with reference to FIGS. 9A-F can be configured to move through a motion transfer mechanism, such as described with reference to FIGS. 10A-C below, or any other suitable mechanism that couples the moving squeegees to a motorized handle.

Figure 10A:
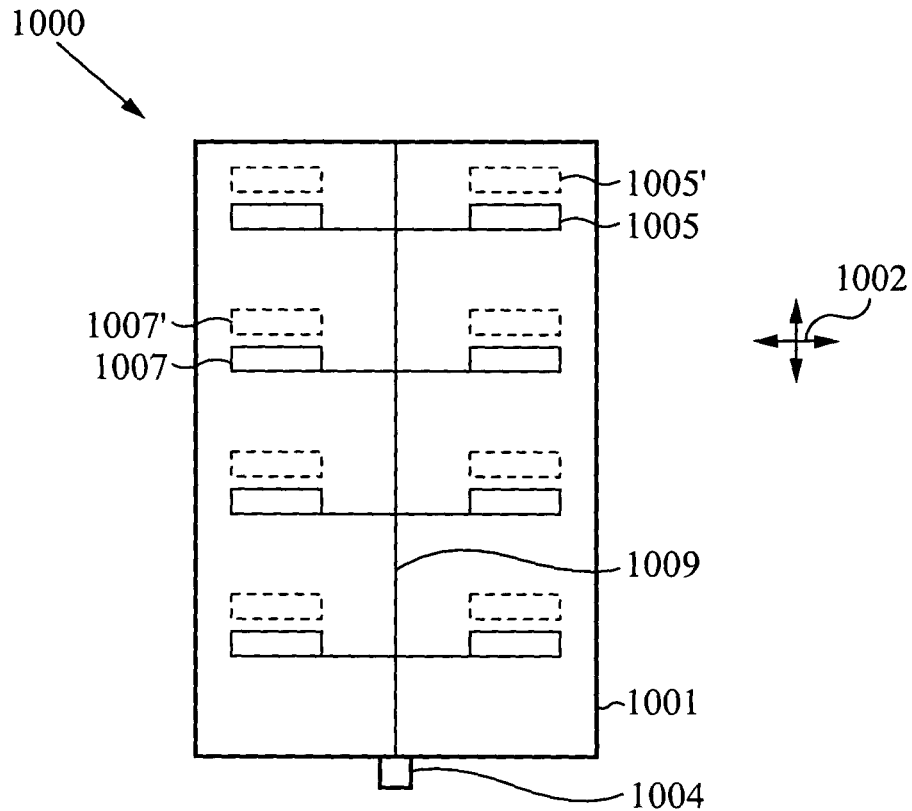
FIGS. 10A-D show schematic top view of squeegee fields that are configured to move separately and in a concerted fashion through a motion transfer mechanism, in accordance with the embodiments of the invention.

Referring now to FIG. 10A, a cleaning head 1000 in accordance with the embodiments of the invention includes squeegee fields 1005 and 1007 that are coupled to a motion transfer mechanism 1009 that is configured to move the squeegee fields 1005 and 1007 back and forth from the positions of the squeegees shown 1005 and 1007 to positions shown by the dotted lines 1005' and 1007'. The cleaning head 1000 also preferably includes means to couple 1004 the cleaning head 1000 to a motorized handle (not shown) that provides the motion to the squeegee fields 1005 and 1007 through the motion transfer mechanism 1009. It will be clear to one skilled in the art from the description above and below that the squeegee fields 1005 and 1007 can be configured to move in any direction or combination of directions as indicated by the arrows 1002.

Figure 10B:
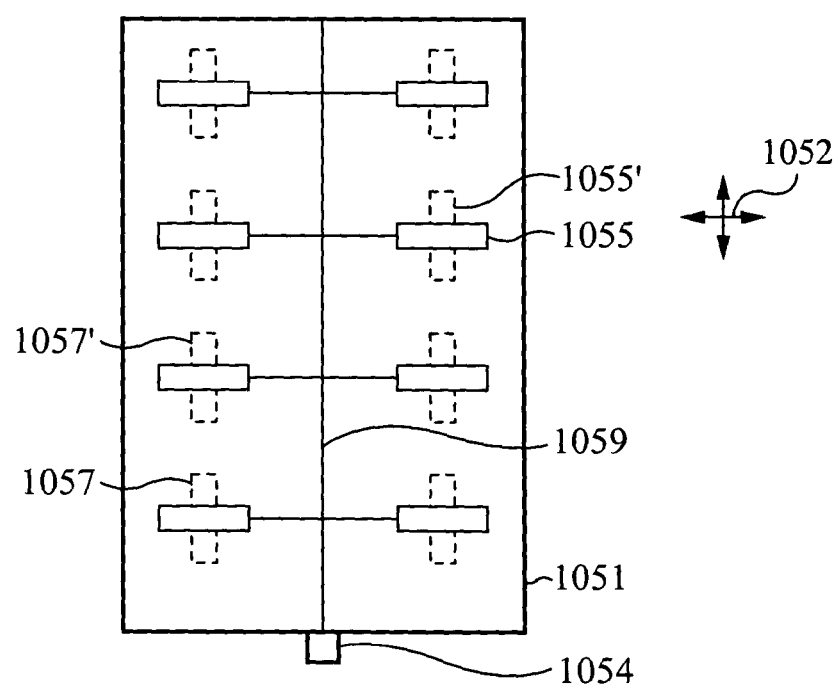

Referring now to FIG. 10B, a cleaning head 1050 in accordance with the embodiments of the invention includes squeegee fields 1055 and 1057 that are coupled to a motion transfer mechanism 1059 that is configured to move the squeegee fields 1005 and 1007 in a rotational motion from the positions of the squeegees shown 1055 and 1057 to positions shown by the dotted lines 1055' and 1057'. The cleaning head 1050 also preferably includes means to couple 1054 the cleaning head 1050 to a motorized handle (not shown) that provides the motion to the squeegee fields 1055 and 1057 through the motion transfer mechanism 1059. It will be clear to one skilled in the art form the description above and below that the squeegee fields 1055 and 1057 can be configured to move in any direction or combination of directions as indicated by the arrows 1052.

Figure 10C:
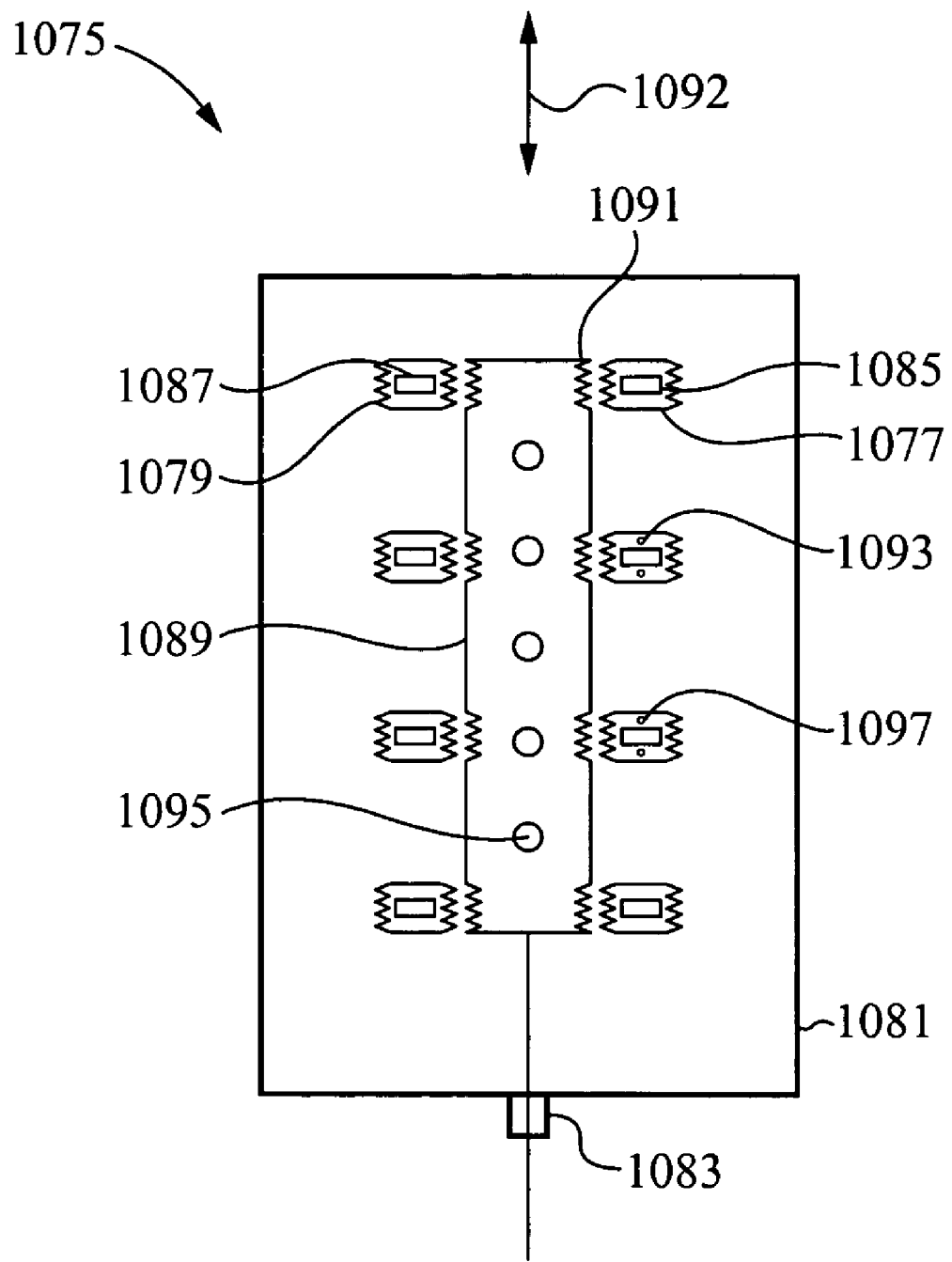

FIG. 10C shows a schematic representation of a cleaning head 1075 in accordance with the embodiments of the invention. The cleaning head 1075 includes squeegee fields 1085 and 1087 that are coupled to a motion transfer mechanism 1089 that is configured to move the squeegee fields 1085 and 1087 in a rotational motion from the positions shown, to the rotational positions 1055' and 1057', similar to those shown in FIG. 10B. The squeegee fields 1085 and 1087, for example, are mounted to, or coupled to, gears 1077 and 1079 are mated to the motion transfer mechanism 1089 through gear teeth 1091. In operation, a motorized handle (not shown) is attached to the cleaning head 1075 through an attachment features 1083 and the motion transfer mechanism 1089 moves in a direction 1092, as indicted by the arrow 1092, thereby causing the squeegee fields 1085 and 1087 to pivotally and separately rotated in and out of the positions shown, such as described above with reference to FIG. 10B. In accordance with further embodiments of the invention, the cleaning head 1075 can also include any number of bristle groups 1093 and/or nodules 1097 that protrude from a support structure 1081 and/or the gears 1077 and 1079. Preferably, the cleaning head 1075 includes bristle groups 1095, nodules and/or squeegees that protrude from the motion transfer mechanism 1087 and move along with the motion transfer mechanism 1089 in the direction 1092.

Figure 10D:
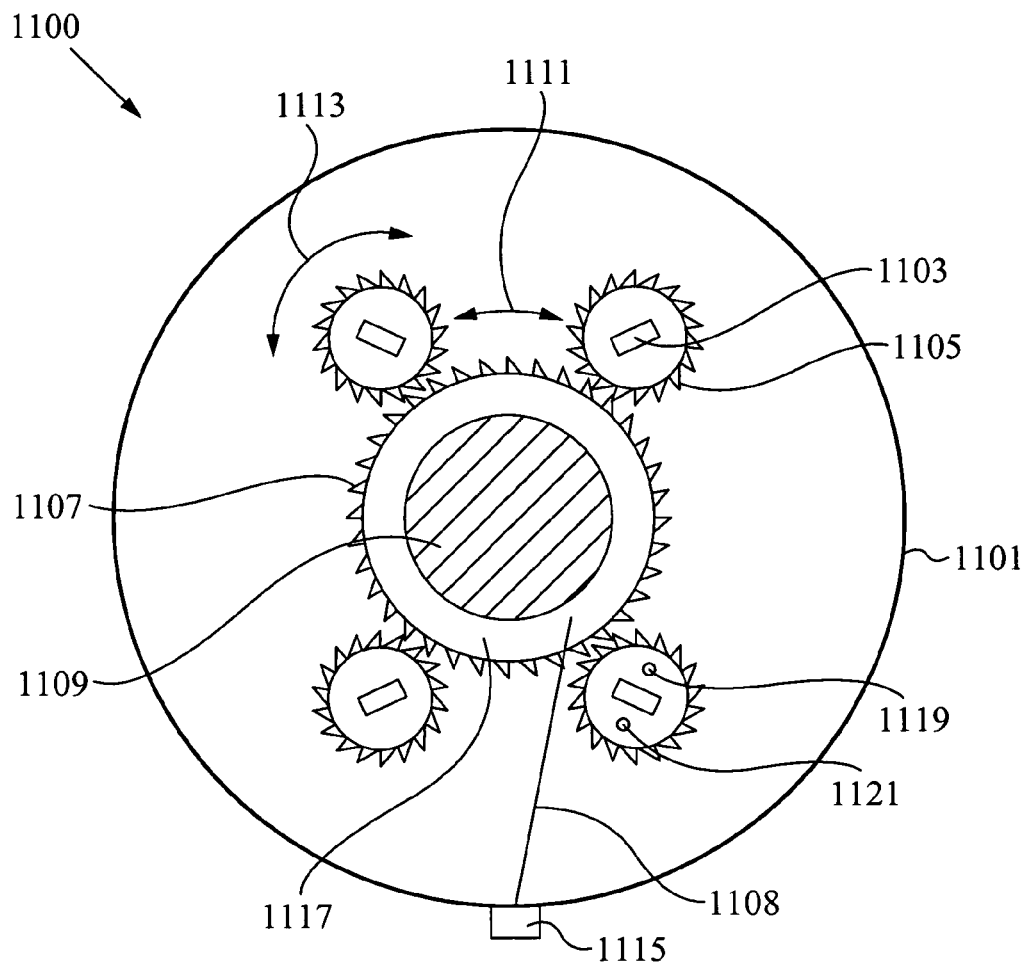

FIG. 10D shows a schematic representation of a cleaning head 1100 in accordance with the embodiments of the invention. The cleaning head 1100 includes squeegees 1103 that are coupled to or protrude from rotatable gear structures 1105. The gear structures 1105 are configured to pivotally rotate or oscillate independently or separately as indicated by the arrow 1113. The gear structures 11 05 can be mated through gear teeth or any other suitable mechanism with a central gear structure 1107. The central gear structure 1107 is configured to pivotally rotate or oscillate independently or separately, as indicated by the arrow 1111. In operation, a motorized handle (not shown) is attached or coupled to the cleaning head 1100 through an attachment feature 1115. Mechanical motion is transferred from the motorized handle to the central gear structure 1107 through an arm structure 1108, or any other suitable structure, thereby causing the central gear structure 1107 to rotate or oscillate. The rational or oscillatory motion of the central gear 1107 is transferred through the gear teeth, or other suitable mechanism, to the gear structures 1105 causing the gear structures 1105 and the squeegees 1103 to rotate or oscillate. In accordance, with further embodiments of the invention the cleaning head 1100 can also include any number of bristle groups and/or nodules 1119 and 1121 that are coupled to, or protruding from, the gear structures 1105 and that also rotate or oscillate along with the gear structures 1105 and the squeegees 1103. Preferably, the cleaning head 1100 includes a bristle group 1109, nodules and/or squeegees that are coupled to, or protrude from, the central gear structure 1109 and that rotated or oscillate along with the central gear structure 1107. It will be clear to one skilled in the art from the description above that the squeegees 1103 can be configured to move independently or separately with any simple or complex motion. For example, the gears structures 1105 can be configured to rotate or oscillate around the central gear structure 1107 in the direction indicated by the arrow 1111 while the gear structures 1105 simultaneously rotate or oscillate in the direction indicated by the arrow 1113.

Figure 11A:
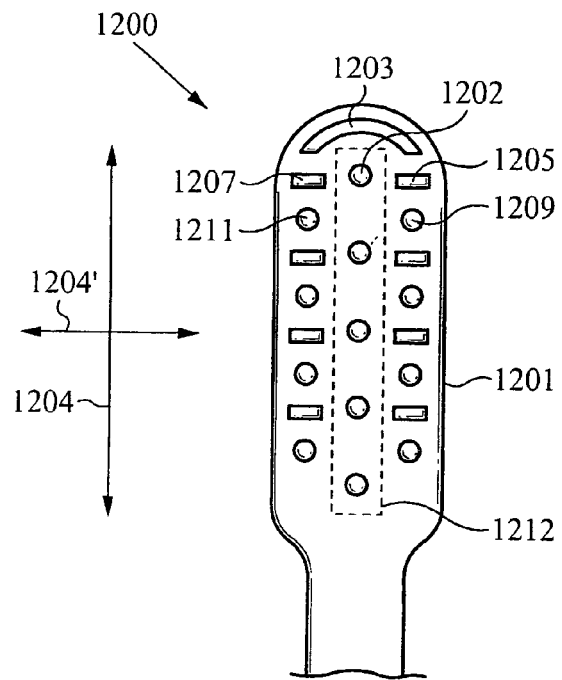
FIGS. 11A-B shows view of a toothbrush with a field of squeegees configured to automatically move, in accordance with the embodiments of the invention.
Figure 11B:
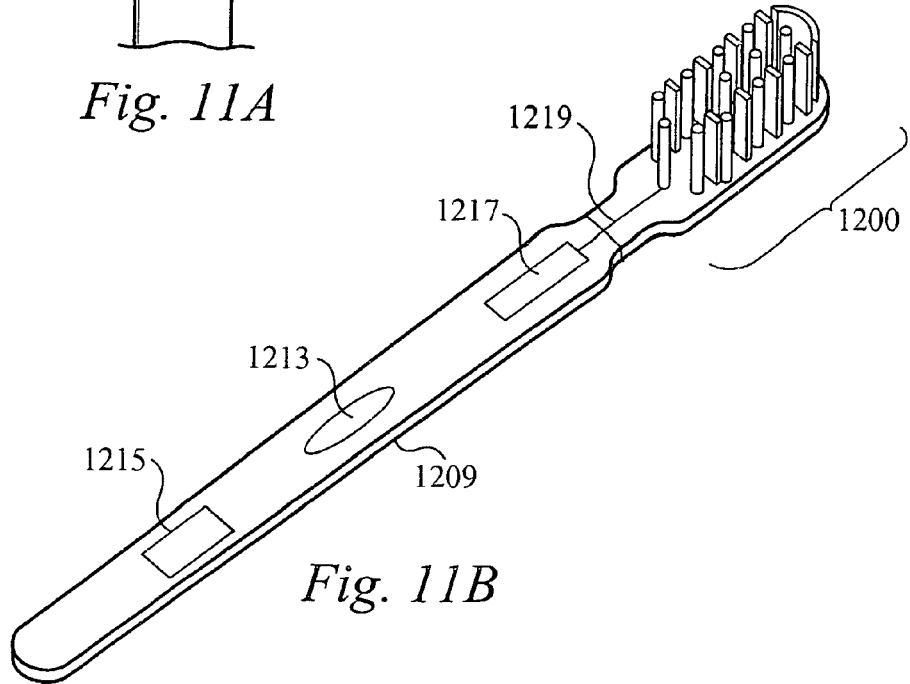

FIGS. 11A-B show a top view and perspective view of a toothbrush with moving squeegee fields, in accordance with the embodiments of the invention. Referring to FIG. 11A, a cleaning head 1200 of the toothbrush includes rows of squeegee elements 1205 and 1207 extend along opposed sides of and protrude from a support structure 1201. The cleaning head 1200 also includes a plurality of bristle groups and/or nodules 1209 and 1211 that protrude from the support structure 1201 at positions between the squeegees within the rows of squeegees 1205 and 1207. The cleaning head 1200 can also include a middle section 1212 with bristles 1202, nodules or a combination thereof protruding therefrom. The cleaning head 1200 can also include any number of curved squeegees protruding from the support structure 1201, such as a curved squeegee 1203 positioned near an edge of the cleaning head 1200. In operation, at least a portion of the rows of squeegees 1205 and 1207 are configured to move. For examples, the portions of the rows of squeegees 1205 and 1207 are configured to move back and forth and parallel to the elongated direction of the cleaning head 1200, as indicated by the arrow 1204, side-to-side and perpendicular to the elongated direction the cleaning head 1200, as indicated by the arrow 1204', move up and down corresponding to a motion in and out of the plane of FIG. 11A, with an oscillating motion, a rotational motion, a vibrating motion or any combination thereof. Preferably, the center section 1212 is also configured to move in a direction that is different from the motion of the squeegees 1205 and 1207. For example, the center section can be configured to vibrate, while the squeegees within the rows 1205 and 1207 oscillate, as described with reference to FIG. 10B.

Referring now to FIG. 11B, the toothbrush includes a powered handle 1209. The powered handle includes a motor 1217 for generating mechanical motion. The toothbrush can include a battery source 1215 for providing power to the motor 1217 and/or the toothbrush can include an external power source and/or a recharging station, such as that described above with reference to FIG. 2. The toothbrush can include a motion transfer mechanism 1219 for transferring mechanical motion generated from the motor 1217 to the squeegees and bristle of the cleaning head 1200. The toothbrush can also include a switch 1213 for turning on and off the toothbrush. The switch 1213 can be a timer switch that is configured to automatically turn off the toothbrush after a preselected time of operation.

It will be clear to one skilled in the art from the description that the system and device of the present invention has applications for cleaning or treating any number of different surfaces. It is also understood that abrasive materials, anti-microbial, antiseptics and/or other materials can be integral with the squeegees and nodules or attached to the walls or edges of squeegees and nodules, as required for the application at hand. Further, it is understood that the squeegee can be formed from any number of different materials and combinations of materials, including porous, textured or absorbent materials. Accordingly, the proceeding preferred embodiments of the invention are set forth without any loss of generality to, and without imposing limitations upon, the claimed invention.

What is claimed is:

1. A device comprising a cleaning head, the cleaning head comprising a squeegee field comprising a plurality of squeegees that each coupled to a separate gear that is mated to a motion transfer mechanism, wherein the plurality of squeegees are configured to move separately and in a concerted fashion relative to a support surface with the support surface stationary, the device further comprising a power handle coupled to the cleaning head for transferring mechanical motion to the plurality of squeegees through the motion transfer mechanism, wherein the cleaning head further includes bristles and wherein the bristles are coupled to a center region of the cleaning head that is configured to move.

2. The device of claim 1, wherein the plurality of squeegees are configured to move up and down, back and forth or side to side relative to the support surface of the cleaning head.

3. The device of claim 1, wherein the plurality of squeegees is configured to vibrate, rotate or oscillate.

4. The device of claim 1, wherein the center region is configured to move up and down, back and forth or side to side relative to the support surface of the cleaning head.

5. The device of claim 1, wherein the center region is configured to vibrate.

6. The device of claim 1, wherein the cleaning head further comprising nodule structures.

7. The device of claim 1, wherein each of plurality of squeegees protrude to form top wiping edges and side wiping edges.

8. A device comprising:
 a) cleaning head comprising:
  i) an array of squeegees coupled to a plurality of separate gears that are mated to a motion transfer mechanism configured to move automatically and separately in at least one direction through the motion transfer mechanism;
  ii) a movable section comprising bristles; and
 b) a motorized handle configured to couple to the cleaning head to transfer mechanical motion from a motor to the motion transfer mechanism.

9. The device of claim 8, wherein the array of squeegees includes one or more rows of linear squeegee segments.

10. The device of claim 8, wherein the squeegees are configured to move back and forth, vibrate, rotate or oscillate.

11. The device of claim 8, wherein the bristles are configured to automatically move with a motion that is different from the squeegees.

12. The device of claim 8, further comprising nodules.

13. A cleaning device comprising:
 a) a movable section comprising bristles; and
 b) rows of movable squeegees wherein the movable squeegees are coupled to separate gears and flank or border the movable section, wherein the movable section and the movable squeegees both move automatically and separately from each other through a motion transfer mechanism coupled to the movable section and separate gears.

14. The device of claim 13, further comprising nodules.

15. The device of claim 13, further comprising a motorized handle.

* * * * *